US005631382A

United States Patent [19]

Tanizawa et al.

[11] Patent Number: 5,631,382

[45] Date of Patent: May 20, 1997

[54] FULGIMIDE COMPOUND

[75] Inventors: Tsuneyoshi Tanizawa; Takashi Kobayakawa, both of Tokuyama, Japan

[73] Assignee: Tokuyama Corporation, Tokuyama, Japan

[21] Appl. No.: 511,365

[22] Filed: Aug. 4, 1995

[30] Foreign Application Priority Data

| | | | |
|---|---|---|---|
| Aug. 8, 1994 | [JP] | Japan | 6-186119 |
| Jun. 26, 1995 | [JP] | Japan | 7-159389 |
| Jun. 28, 1995 | [JP] | Japan | 7-161837 |

[51] Int. Cl.[6] .......... C07D 209/96

[52] U.S. Cl. .......... 548/407

[58] Field of Search .......... 548/429, 430, 548/431, 439, 407

[56] References Cited

FOREIGN PATENT DOCUMENTS

| | | |
|---|---|---|
| 0316179 | 5/1989 | European Pat. Off. . |
| 0351112 | 1/1990 | European Pat. Off. . |
| 0629626 | 12/1994 | European Pat. Off. . |

*Primary Examiner*—Joseph McKane
*Assistant Examiner*—Richard S. Myers, Jr.
*Attorney, Agent, or Firm*—Sherman and Shalloway

[57] ABSTRACT

A fulgimide compound which reversibly changes from a colorless state into a colored state upon the action of light including ultraviolet-rays, and a composition containing this compound. The fulgimide compound is represented by the following formula (I),

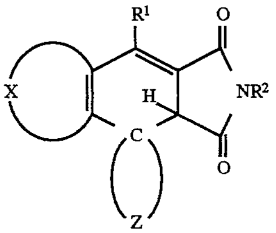

(I)

wherein the following formula (a)

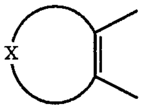

represents a divalent aromatic hydrocarbon or a divalent unsaturated heterocyclic group which may have a substituent, respectively, $R^1$ represents a monovalent hydrocarbon group or a monovalent heterocyclic group which may have a substituent, respectively, and the following formula (b),

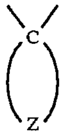

represents a norbornylidene group, bicyclo[3,3,1] nonylidene group or adamantylidene group which may have a substituent, respectively, and $R^2$ is a perhalogenoalkyl group, cyano group, alkoxycarbonyl group that may have a substitutent, alkylcarbonyl group that may have a substituent, arylcarbonyl group that may have a substituent, nitro group, sulfonyl group, alkylsulfonyl group that may have a substituent, arylsulfonyl group that may have a substituent or aryloxycarbonyl group that may have a substituent.

7 Claims, 1 Drawing Sheet

FULGIMIDE COMPOUND

BACKGROUND OF THE INVENTION

1. Field of the Invention

The present invention relates to a novel fulgimide compound having photochromic action, to a composition containing the same compound and to the use thereof. More specifically, the invention relates to a novel fulgimide compound having excellent durability which changes from a colorless state into a colored state upon the action of light that contains ultraviolet rays such as of the sun light or the mercury lamps, the change being reversible, to a composition containing the same compound and to the use thereof.

2. Description of the Prior Art

Photochromism is a phenomenon which is drawing attention in these several years and is a reversible action exhibited by certain compounds. That is, a compound quickly changes its color when it is irradiated with the sun light or the light containing ultraviolet rays such as of a mercury lamp and returns to the original color when it is no longer irradiated with the light and is placed in a dark place. The compound having this property is called photochromic compound, and compounds having various structures have heretofore been synthesized and proposed without, however, any common skeleton among their structures.

Under such circumstances, a fulgide compound or a fulgimide compound disclosed in Japanese Laid-Open Patent Publication No. 28154/1990 and represented by the following general formula

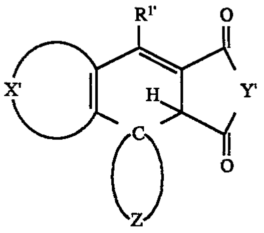

exhibits no color and remains stable in a general state but readily develops color upon irradiation with the sun light or ultraviolet rays, returns to the colorless state when it is no longer irradiated with the light, and is, hence, a compound having excellent photochromic property making it possible to repeat these changes in color maintaining good durability. In the fulgide compound or fulgimide compound, X

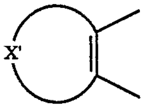

stands for an aromatic hydrocarbon group or an unsaturated heterocyclic group, and $R^{1'}$ stands for a hydrocarbon group or a heterocyclic group. Moreover, Y' stands for an oxygen atom, an imide group, or a group in which a hydrogen atom of the imide group is substituted by a group to which is bonded an electron-releasing group of an alkyl group or an aryl group or to which is bonded an electron-withdrawing group of a cyano group or an alkoxycarbonyl group via an alkylene group or an alkylidene group. Furthermore,

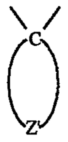

represents a norbornylidene group or an adamantylidene group which may have a substituent.

It has been considered that the fulgimide compound which has a rigid cage-like adamantylidene group or a norbornylidene group without distortion, weakens a single bond that constitutes a part of a six-membered ring, facilitates electron-cyclic ring cleavage upon irradiation with the light containing ultraviolet rays, and, as a result, assumes a color-producing form. As a maximum absorption wavelength is lengthened, however, these compounds develop a defect in that they have already been exhibiting yellowish color (hereinafter often referred to as initial coloring) before they are being irradiated with ultraviolet rays. When these compounds are used for a photochromic lens or the like, therefore, the lens at first exhibits a yellow color.

In such circumstances, therefore, it has been urged to develop a photochromic compound suppressing the initial coloring despite a maximum absorption wavelength is lengthened.

SUMMARY OF THE INVENTION

The object of the present invention is to provide a novel fulgimide compound.

Another object of the present invention is to provide a compound which changes from a colorless state into a colored state or a densely colored state upon irradiation with the light such as sun light or light containing ultraviolet-rays such as of a mercury lamp, the change being reversible.

A further object of the present invention is to provide a fulgimide compound which suppresses initial coloring.

A still further object of the present invention is to provide a highly practicable fulgimide compound.

Yet further object of the present invention is to provide a process which is industrially advantageous for producing a fulgimide compound.

Furthermore, the object of the present invention is to provide a high molecular composition containing a fulgimide compound.

The above-mentioned objects of the present invention will become obvious from the following description.

These objects of the present invention are accomplished by a novel fulgimide compound represented by the following formula (I),

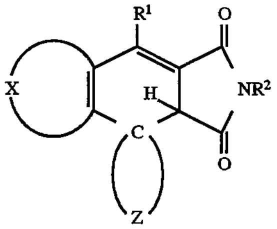

(I)

wherein the following formula (a)

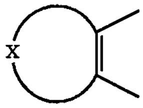

represents a divalent aromatic hydrocarbon or a divalent unsaturated heterocyclic group which may have a substituent, respectively, $R^1$ represents a monovalent hydrocarbon group or a monovalent heterocyclic group which may have a substituent, respectively, and the following formula (b),

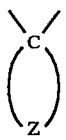

represents a norbornylidene group, bicyclo [3,3,1] nonylidene group or adamantylidene group which may have a substituent, respectively, and $R^2$ is a perhalogenoalkyl group, cyano group, alkoxycarbonyl group that may have a substituent, alkylcarbonyl group that may have a substituent, arylcarbonyl group that may have a substituent, nitro group, sulfonyl group, alkylsulfonyl group that may have a substituent, arylsulfonyl group that may have a substituent or aryloxycarbonyl group that may have a substituent.

DETAILED DESCRIPTION OF THE INVENTION

Figure 1:
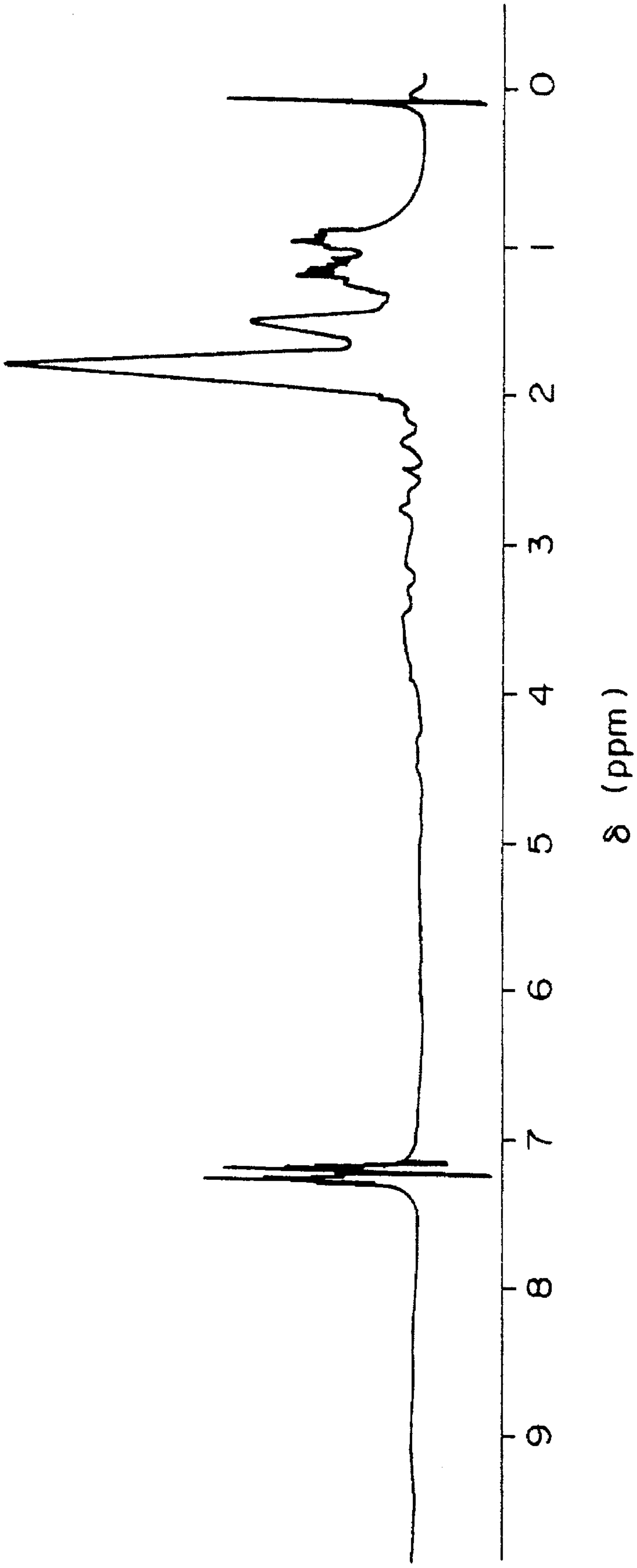
FIG. 1 is an $^1$H-NMR chart of a compound obtained in Example 1.

In the above-mentioned general formula (I) of the present invention, the group of the formula (a) is an aromatic hydrocarbon group or unsaturated heterocyclic group which may have a substituent, respectively. These groups may usually have up to five substituents and, preferably, up to three substituents. The aromatic hydrocarbon group has 6 to 20 carbon atoms and, preferably, 6 to 14 carbon atoms. Examples of the ring that forms the aromatic hydrocarbon ring include a benzene ring, naphthalene ring, phenanthrene ring, etc.

Examples of the unsaturated heterocyclic ring include a mono-heterocyclic group of a five-membered ring or a six-membered ring containing at least one kind of hetero atom such as nitrogen atom, oxygen atom or sulfur atom in a number of one, or a condensed heterocyclic group of a form made up of the above-mentioned groups with which a benzene ring or a cyclohexene ring is condensed. Examples of the ring forming heterocyclic groups include nitrogen-containing heterocyclic rings such as pyrrole ring, pyridine ring, quinoline ring, isoquinoline ring, and indole ring; oxygen-containing heterocyclic rings such as furan ring, benzofuran ring, pyran ring, and tetrahydrobenzofuran ring; and sulfur-containing heterocyclic ring such as thiophene ring, benzothiophene ring, and tetrahydrobenzothiophene ring.

Examples of the substituents that may be possessed by the aromatic hydrocarbon group or the unsaturated heterocyclic group represented by the above-mentioned formula (a) include halogen atoms such as fluorine, chlorine, bromine and iodine; hydroxyl group; cyano group; nitro group; amino group; carboxyl group; alkylamino group having 1 to 4 carbon atoms such as methylamino group and diethylamino group; alkyl groups having 1 to 4 carbon atoms such as methyl group, ethyl group, propyl group and t-butyl group; halogenalkyl group having 1 to 3 halogen atoms such as 2-chloroethyl group and trifluoromethyl group; lower alkoxy group having 1 to 4 carbon atoms such as methoxy group, ethoxy group and t-butoxy group; aryl groups having 6 to 10 carbon atoms such as phenyl group, naphthyl group and toluyl group; aryloxy groups having 6 to 14 carbon atoms such as phenoxy group, and 1-naphthoxy group; aralkyl groups having 7 to 15 carbon atoms such as benzyl group, phenylethyl group and phenylpropyl group; aralkoxy groups having 7 to 15 carbon atoms such as benzyloxy group and phenylpropoxy group; and alkylthio groups having 1 to 4 carbon atoms. These substituents may be the same or different, and there is no particular limitation in their positions.

It is desired that the group represented by the above-mentioned formula (a) is an aromatic hydrocarbon group or an unsaturated heterocyclic group which, in its respective cases, may be replaced by at least one atom or group selected from the group consisting of halogen atom, nitro group, alkylthio group having 1 to 4 carbon atoms, alkyl group having 1 to 4 carbon atoms and alkoxy group having 1 to 4 carbon atoms.

More desirably, the group represented by the above-mentioned formula (a) is an aryl group having 6 to 14 carbon atoms which, in its respective cases, may be replaced by 1 to 3 substituents, or a five-membered or six-membered mono- heterocyclic group having nitrogen atom, oxygen atom or sulfur atom, or a condensed heterocyclic group in which the heterocyclic ring group is condensed with a benzene ring or a cyclohexene ring.

It is further desired that the group represented by the above-mentioned formula (a) is a benzene ring, a five-membered or six-membered mono- or heterocyclic ring having 1 to 3 hetero atoms, or a condensed heterocyclic ring of a form in which the above heterocyclic ring is condensed with a benzene ring or a cyclohexene ring. Preferably, these benzene ring, mono- heterocyclic ring or condensed heterocyclic ring may contain 1 or 2 substitutents that are mentioned above.

In the above-mentioned general formula (1), $R^1$ is a monovalent hydrocarbon group or a monovalent heterocyclic ring group that may have a substituent. Any widely known hydrocarbon group or a heterocyclic group may be used without any limitation. The hydrocarbon group may be any one of the aliphatic group, alicyclic group or aromatic hydrocarbon. Concrete examples include alkyl groups having 1 to 20 and, preferably, 1 to 6 carbon atoms such as methyl group, ethyl group, propyl group and butyl group; aryl groups having 6 to 14 carbon atoms such as phenyl group, toluyl group, xylyl group and naphthyl group; and cycloalkyl groups having 3 to 7 carbon atoms such as cyclopropyl group, cyclobutyl group and cyclopentyl group and, particularly, cyclopropyl group.

Though there is no particular limitation, the heterocyclic group will preferably be a five-membered or six-membered mono- heterocyclic group containing at least one kind of hetero atoms such as nitrogen atom, oxygen atom or sulfur atom in a number of 1 to 3. Preferred examples of the ring forming the heterocyclic group include nitrogen-containing unsaturated heterocyclic rings such as pyrrole ring, pyridine ring, etc.; oxygen-containing unsaturated heterocyclic rings such as furan ring, pyran ring, etc.; and sulfur-containing unsaturated heterocyclic rings such as thiophene ring, etc. It is also allowable to use saturated heterocyclic groups such as saturated piperidine ring, piperazine ring, morpholine ring, pyrrolidine ring, indoline ring and chroman ring.

Concrete examples of the substituents for the groups represented by $R^1$ will be those substituents explained with reference to the formula (a), and the number thereof may be one or more.

In the above-mentioned general formula (I) of the present invention, the group represented by the formula (b) is a norbornylidene group, bicyclo[3,3,1]nonylidene group or adamantylidene group which may have a substituent, respectively. A preferred example of norbornylidene group is a 7-norbornylidene group represented by the following formula (c)

a preferred example of bicyclo[3,3,1]nonylidene group is a bicyclo[3,3,1]9-nonylidene group represented by the following formula (d)

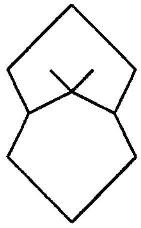

and a preferred example of adamantylidene group is a 2-adamantylidene group represented by the following formula (e)

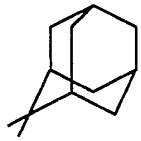

The above formulas represent skeletal structures of the 7-norbornylidene group, bicyclo[3,3,1]9-nonylidene group or 2-adamantylidene group without having substituent.

In the 7-norbornylidene group, bicyclo[3,3,1]9-nonylidene group or 2-adamantylidene group, a hydrogen atom in the above-mentioned formula may be substituted by a substituent and its number may be one or more. When the group has a substituent, the kind, number and position thereof are arbitrarily selected depending upon the object and application. When the group has a plurality of substituents, furthermore, the substituents may be of the same kind or of different kinds. When the group has a plurality of substituents, furthermore, the substituents may be of the same kind or of different kinds.

As substituents for the 7-norbornylidene group, bicyclo [3,3,1]9-nonylidene group or 2-adamantylidene group, there can be exemplified hydroxyl groups; alkylamino groups having 1 to 4 carbon atoms such as methylamino group and diethylamino group; alkoxy groups having 1 to 4 carbon atoms such as methoxy group, ethoxy group and tert-butoxy group; aralkoxy groups having 7 to 15 carbon atoms such as benzyloxy group; aryloxy groups having 6 to 14 carbon atoms such as phenoxy group, 1-naphthoxy group; alkyl groups having 1 to 4 carbon atoms such as methyl group, ethyl group and t-butyl group; halogen atoms such as fluorine, chlorine and bromine; cyano group; carboxyl group; alkoxycarbonyl group having 2 to 10 carbon atoms such as ethoxycarbonyl; alkyl groups substituted with halogen and having 1 or 2 carbon atoms such as trifluoromethyl group; nitro group; aryl groups having 6 to 10 carbon atoms such as phenyl group and toluyl group; and aralkyl groups having 7 to 9 carbon atoms such as phenyl group, ethyl group and phenylpropyl group.

Among these substituents, what are particularly preferred are halogen atoms, alkyl groups having 1 to 4 carbon atoms and alkoxy groups having 1 to 4 carbon atoms.

In the above-mentioned general formula (I) of the present invention, $R^2$ is a perhalogenoalkyl group, cyano group, alkoxycarbonyl group that may have a substituent, alkylcarbonyl group that may have a substituent, arylcarbonyl group that may have a substituent group, nitro group, sulfonyl group, alkylsulfonyl group that may have a substituent, arylsulfonyl group that may have a substituent or aryloxycarbonyl group that may have a substituent. These groups are all electron-withdrawing groups. According to the present invention, a particular electron-withdrawing group is directly bonded to the imide group that constitutes the fulgimide compound, so that the initial coloring of the fulgimide compound is markedly decreased.

Among the groups represented by $R^2$, examples of the perhalogenoalkyl group include perhalogenoalkyl groups having 1 to 4 carbon atoms such as trichloromethyl group, trifluoromethyl group, pentafluoroethyl group, heptafluoropropyl group and nonafluorobutyl group; examples of the alkoxycarbonyl group include alkoxycarbonyl groups having 2 to 5 carbon atoms such as methoxycarbonyl group, ethoxycarbonyl group, propoxycarbonyl group, butoxycarbonyl group and t-butoxycarbonyl group; examples of the alkylcarbonyl group include alkylcarbonyl groups having 2 to 5 carbon atoms such as methylcarbonyl group, ethylcarbonyl group, propylcarbonyl group, butylcarbonyl group and t-butylcarbonyl group; examples of the arylcarbonyl group include arylcarbonyl groups having 7 to 11 carbon atoms such as benzoyl group and 1-naphthylcarbonyl group; examples of the alkylsulfonyl group include alkylsulfonyl groups having 1 to 4 carbon atoms such as methylsulfonyl group, ethylsulfonyl group, propylsulfonyl group and t-butylsulfonyl group; examples of the arylsulfonyl group include arylsulfonyl groups having 6 to 10 carbon atoms such as phenylsulfonyl group and naphthylsulfonyl group; and examples of the aryloxycarbonyl group include arylsulfonyl groups having 7 to 11 carbon atoms such as phenoxycarbonyl group, naphthoxycarbonyl group and the like.

Among the groups represented by $R^2$, substituents for the alkoxycarbonyl group, alkylcarbonyl group, arylcarbonyl group, alkylsulfonyl group, arylsulfonyl group and aryloxycarbonyl group may concretely be those which were described with reference to the aforementioned formula (a), and the number thereof may be one or more. In particular, the group having a substituent is preferably the one that is substituted by a halogen atom or a cyano group. Furthermore, the group substituted by halogen atom is preferably the one in which the alkoxy group, alkyl group or aryl group thereof is entirely substituted by the halogen atom. Examples of such a substituent include perhalogenoalkoxycarbonyl group having 2 to 5 carbon atoms such as trichloromethoxycarbonyl group, trifluoromethoxycarbonyl group, pentafluoroethoxycarbonyl group, heptafluoropropoxycarbonyl group and nonafluorobutoxycarbonyl group; perhalogenoalkylcarbonyl groups having 2 to 5 carbon atoms such as trichloromethylcarbonyl group, trifluoromethylcarbonyl group, pentafluoroethylcarbonyl group, heptafluoropropylcarbonyl group, and nonafluorobutylcarbonyl group; and perhalogenoarylcarbonyl groups having 7 to 11 carbon atoms such as pentafluorobenzoyl group and the like.

In the general formula (I), it is desired that the group represented by the formula (b) is the 7-norbornylidene group, bicyclo[3,3,1]9-nonylidene group or 2-adamantylidene group which may have a substituent, and that $R^2$ is the cyano group, perhalogenoalkylcarbonyl group, alkylcarbonyl group which may have a substituent, arylcarbonyl group which may have a substituent, and, particularly, cyano group or arylcarbonyl group which may have a substituent, from the standpoint of suppressing the initial coloring of the obtained compound.

When $R^2$ is the cyano group, the fulgimide compound that is obtained can be used as a photochromic compound for developing color and extinguishing color reversibly and repetitively maintaining durability superior to that of other fulgimide compounds having a comparable maximum absorption wavelength at the time of developing color.

Exemplified below are fulgimide compounds represented by the above-mentioned formula (1) that can be preferably used in the present invention.

(1) N-Cyano-4-cyclopropyl-6,7-dihydrospirobenzothiophenedicarboxyimide-7,2'-tricyclo[$3.3.1.1^{3,7}$]decane, (2) N-Acetyl-4-cyclopropyl-6,7-dihydrospirobenzothiophenedicarboxyimide-7,2'-tricyclo[$3.3.1.1^{3,7}$]decane, (3) N-Benzoyl-4-cyclopropyl-6,7-dihydrospirobenzothiophenedicarboxyimide-7,2'-tricyclo[$3.3.1.1^{3,7}$]decane, (4) N-Acetyl-4-cyclopropyl-6,7-dihydro-2-methylspirobenzothiophenedicarboxyimide-7,2'-tricyclo[$3.3.1.1^{3,7}$]decane, (5) N-Cyano-6,7-dihydro-4-methyl-2-phenylspirobenzothiophenedicarboxyimide-7,2'-tricyclo[$3.3.1.1^{3,7}$]decane, (6) 5'-Chloro-6,7-dihydro-N-methyl-N'-methylsulfonyl-4-isopropylspiroindoledicarboxyimide-7,2'-tricyclo [$3.3.1.1^{3,7}$]decane, (7) 3',5'-Dichloro-3,4-dihydro-1-ethyl-7-methoxy-N-trichloromethylcarbonylspirodibenzo[5,6-b:d] thiophenedicarboxyimide-4,2'-tricyclo[$3.3.1.1^{3,7}$] decane, (8) N-Benzoyl-3,4-dihydro-5'-methyl-1-(p-methoxyphenyl)spirobenzo[5,6-b:d] furandicarboxyimide-4,2-tricyclo[$3.3.1.1^{3,7}$]decane, (9) 4-Cyclopropyl-5'-methoxy-N'-phenyl-N-trichloromethylcarbonylspirobenzo[b] indoledicarboxyimide-4,2'-tricyclo[$3.3.1.1^{3,7}$]decane, and

(10) 1-Cyclopropyl-3,4-dihydro-N-phenylsulfonyl(6,7,8,9-tetrahydrodibenzo[5,6-b:d] thiophenedicarboxyimide-4,2'-tricyclo[$3.3.1.1^{3,7}$] decane.

The fulgimide compound represented by the above-mentioned general formula (I) of the present invention usually exists as a pale-yellow solid at normal temperature, and can be confirmed by the following means (a) to (c).

(a) The kind and number of protons present in the molecules can be learned by measuring a proton nuclear magnetic resonance spectrum ($^1$H-NMR). That is, a peak due to aromatic proton appears near δ7 to 8 ppm and a broad peak appears near δ1.2 to 2.5 ppm due to a group in which $R^1$ is a cycloalkyl group, and due to a norbornylidene group, a bicyclo[3.3.1]nonylidene group or adamantylidene group. By comparing their δ peak intensities, 5 furthermore, it is allowed to know the number of protons in the bound groups.

(b) Percentage by weight of carbon, hydrogen, nitrogen, sulfur and halogen can be found by elemental analysis. By subtracting the sum of the elements (% by weight) that is found from 100, furthermore, it is allowed to calculate the amount of oxygen (% by weight). It is therefore possible to determine the composition of the corresponding product.

(c) By measuring the $^{13}$C-nuclear magnetic resonance spectrum ($^{13}$C-NMR), it is allowed to know the kind of carbon present in the molecules. A peak appears near δ27 to 52 ppm due to a group in which $R^1$ is a cycloalkyl group, and due to a norbornylidene group, a bicyclo[3.3.1]nonylidene group or an adamantylidene group, and a peak appears near δ110 to 150 ppm due to carbon >C=0.

The fulgimide compound of the above-mentioned general formula (I) of the present invention may be produced by any process, and no limitation is imposed on the kind of the process for its preparation. Described below, however, is a preferred and representative process to which only the present invention is in no way limited. The fulgimide compound can be produced by, for example, the following process A. Process A:

According to this process A, a fulgimide compound represented by the above-mentioned general formula (I) is prepared by reacting an acid anhydride represented by the following general formula (II)

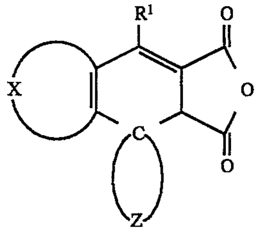

(II)

wherein

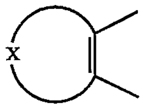

,

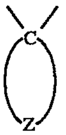

and $R^1$ are as defined in the above-mentioned general formula (I), with amines represented by the following formula (III)

$$H_2N—R^2 \quad \text{(III)}$$

wherein $R^2$ is as defined in the above-mentioned general formula (I), followed by cyclization.

It is desired that the reaction in this process A is carried out in a solvent which is a nonprotonic polar solvent such as N-methylpyrrolidone, dimethylformamide, tetrahydrofuran or 1,4-dioxane.

In the method in which the acid anhydride of the above general formula (II) is reacted with the amine compound and is then cyclized, it is desired to effect the heating at, for example, 160° to 220° C., or to effect this heating in combination with irradiation with ultraviolet rays, or to bring the reaction system into contact with a Lewis acid catalyst. As the Lewis acid catalyst, a known compound such as $SnCl_4$, $TiCl_4$, $SbCl_5$ or $AlCl_3$ can be used without any limitation. Though there is no particular limitation, it is desired to use the Lewis acid catalyst in an amount of usually from 0.001 to 1 mole per mole of the compound that is to be cyclized.

In the process A, furthermore, when the acid anhydride of the general formula (II) is to be reacted with the amine compound, the reaction ratio may be selected over a wide range but is usually from 1:10 to 10:1 and, preferably, from 1:5 to 5:1 in terms of a molar ratio.

The above reaction is carried out usually under the conditions of a temperature of from 25° to 160° C. and a time of from 1 to 24 hours. After the reaction, the solvent is removed, the reaction product is dehydrated with a dehydrating agent such as acetyl chloride or anhydrous acetic acid, and the obtained compound is subjected to the cyclization reaction under the above-mentioned conditions to obtain a fulgimide compound of the present invention.

In the process A, the acid anhydride represented by the above-mentioned general formula (II) used as a starting material can be prepared by, for example, the following method.

That is, a carbonyl compound represented by the following general formula (IIa)

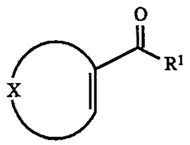

(IIa)

wherein

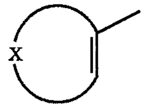

and $R^1$ are as defined in the above-mentioned general formula (I), and a derivative of diester of succinic acid represented by the following general formula (IIb)

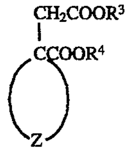

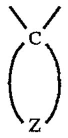

is as defined in the above-mentioned general formula (I), and $R^3$ and $R^4$ are the same or different alkyl groups having 1 to 6 carbon atoms, are subjected to the condensation reaction followed by the processing that will be described later, to obtain an acid anhydride represented by the above-mentioned general formula (II).

In the above-mentioned condensation reaction, the reaction ratio of the carbonyl compound of the general formula (IIa) and the derivative of diester of succinic acid of the general formula (IIb) is selected from a wide range but is generally selected to be 1:10 to 10:1 and, preferably, 1:5 to 5:1. The reaction is usually carried out at 0° C. to 110° C. and, preferably, at 10° C. to 100° C. It is desired that the reaction is carried out by using a solvent which may be a non-protonic solvent such as benzene, diethyl ether, toluene or tetrahydrofuran.

The condensation reaction is usually carried out in the presence of a condensing agent such as sodium hydride, t-butoxide, sodium ethylate, etc. The condensing agent is used in an amount of usually from 0.1 to 10 moles per mole of the carbonyl compound of the above-mentioned general formula (IIa).

After the reaction, the obtained diester of dicarboxylic acid is converted into a free dicarboxylic acid. This reaction is carried out under the conditions of a hydrolysis reaction in the presence of a base that has been widely known. The reaction is carried out by using, for example, a sodium hydroxide solution containing 10% of ethanol at a temperature of from 0° to 80° C.

The thus obtained dicarboxylic acid is converted into an acid anhydride according to a method that has been widely known; i.e., the acid anhydride of the above-mentioned general formula (II) is thus obtained. The reaction for obtaining the acid anhydride is carried out by using a widely known reagent such as anhydrous acetic acid or acetyl chloride. Process B:

According to this process B, a fulgimide compound represented by the above-mentioned general formula (I) is prepared by reacting an imide compound represented by the following general formula (IV)

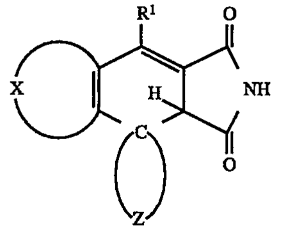

(IV)

wherein

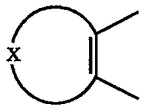

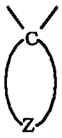

and $R^1$ are as defined in the above-mentioned general formula (I), with an alkali metal, followed by the reaction with a halogen compound represented by the following formula (V)

$A—R^2$ wherein $R^2$ is as defined in the above-mentioned formula (I), and A is a halogen atom.

The alkali metal used in this process B may be a metal sodium, a metal potassium or a metal lithium. The reaction ratio of the alkali metal is usually selected over a range of from 1.0 to 10 moles per mole of the imide compound represented by the above-mentioned general formula (IV). It is further desired that the reaction ratio of the halogen compound is selected over a range of from 0.5 to 10 moles per mole of the compound that is obtained by reacting an alkali metal.

The solvent used in this reaction is the one which is the same as the one that was described with reference to the above-mentioned process A. Preferably, the reaction temperature is usually from 0° to 100° C.

The fulgimide compound of the above-mentioned general formula (I) of the present invention can be obtained by either the above-mentioned process A or the process B or by a modification thereof.

The fulgimide compound of the above-mentioned general formula (I) of the present invention usually exhibits orange to bluish color tone when it develops color. When a desired color is not obtained from this compound that is used as a photochromic compound, therefore, it is desired to use it being mixed with a photochromic compound having other color tone.

In such a case, a chromene compound can be favorably used as the other photochromic compound. That is, the chromene compound usually develops orange to yellowish color tone. By mixing it to the fulgimide compound of the above-mentioned general formula (I), therefore, there can be obtained such colors as grey, amber, brown, as well as various other intermediate color tones.

The chromene compound has a chromene skeleton. Any widely known compound having photochromic property can be used without any limitation. In particular, a chromene compound represented by the following general formula (VI) can be favorably used,

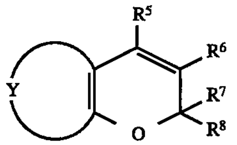

(VI)

wherein $R^5$, $R^6$, $R^7$ and $R^8$ may be the same or different and are hydrogen atoms, hydrocarbon groups, substituted amino groups, aromatic hydrocarbon groups, unsaturated heterocyclic groups or saturated heterocyclic groups which may have a substituent, and $R^7$ and $R^8$ in combination may form a ring, and

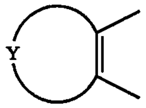

is an aromatic hydrocarbon group or an unsaturated heterocyclic group which may have a substituent, respectively.

It is desired that in the above formula (VI), $R^5$, $R^6$, $R^7$ and $R^8$ are hydrogen atoms, alkyl groups, aryl groups, substituted amino groups or saturated heterocyclic ring groups. Here, the alkyl group and aryl group may be those described with reference to the aforementioned formula (I), the substituted amino group may be the one in which at least one hydrogen atom is substituted in the alkyl group and in the aryl group, and the saturated heterocyclic ring group may be a monovalent group derived from a five- to six-membered ring that contains one to two nitrogen atoms, oxygen atoms or sulfur atoms such as of pyrrotidine ring, imidazoline ring, piperidine ring, piperazine ring or morpholine ring, as ring-constituting atoms.

In the above formula (VI), a ring formed by $R^7$ and $R^8$ in combination will be a norbornylidene group, a bicyclo (3.3.1)nonylidene group, etc.

In the above formula (VI), furthermore, the aromatic hydrocarbon groups or the unsaturated heterocyclic ring groups represented by

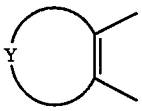

are the same as the groups described in the above-mentioned formula (I). Though there is no particular limitation, the substituent of these groups will be, for example, a halogen atom such as chlorine, bromine or iodine; an alkyl group having 1 to 20 carbon atoms such as methyl group or ethyl group; an alkoxy group having 1 to 20 carbon atoms such as methoxy group or ethoxy group; an aryl group having 6 to 10 carbon atoms such as phenyl group, tolyl group or xylyl group; an amino group; a nitro group; a cyano group and the like group.

Among the chromene compounds represented by the above-mentioned general formula (VI), preferred compounds are those in which $R^5$ and $R^6$ are both hydrogen atoms, $R^7$ and $R^8$ are alkyl groups, respectively, or in combination are forming a bicyclo(3.3.1)nonylidene group or a norbornylidene group, and

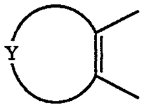

is a naphthalene ring which may be substituted, from the standpoint of photochromic property.

Concretely described below are the chromene compounds that can be favorably used in the present invention.

Chromene compounds:

(1) Spiro(norbornane-2,2'-(2H)benzo(h)chromene), (2) Spiro(bicyclo[3.3.1]nonane-9,2'-(2H)benzo(h) chromene)

(3) 7'-Methoxyspiro(bicyclo(3,3,1)nonane-9,2'-(2H) benzo(h)chromene), (4) 7'-Methoxyspiro(norbornane-2,2'-(2H)benzo(f) chromene), (5) 2,2-Dimethyl-7-octoxy(2H)benzo(h)chromene), (6) 4'-Methylspiro(bicyclo(3,3,1)nonane-9,2'-(2H)benzo (h)chromene), (7) 3'-Methylspiro(bicyclo(3.3.1)nonane-9,2'-(2H)benzo (h)chromene), (8) Spiro(tricyclo[3.3.1.$1^{3.7}$]decane-2,2'-(2H)benzo(h) chromene), (9) 4'-Piperidinospiro(bicyclo(3.3.1)nonane-9,2'-(2H) benzo(h)chromene),

(10) 2,2-Dimethyl-6-octoxy(2H)benzo(h)chromene),

(11) Spiro(norbornane-2,2'-(2H)naphtho-(1,2-h) chromene),

(12) 2,2-Dimethyl-7-(ethylthiohexyl)oxy(2H)benzo(h) chromene),

(13) 6-Chloro-2,2-dimethyl-7-(diisopropylphosphorohexyl)oxo(2H)benzo(h) chromene,

(14) 2,2-Dimethyl(2H)pyrido(2,3-h)chromene,

(15) 7-Methoxy-2,2-dimethyl(2H)benzo(h)chromene, and

(16) 7-(Diethylaminooctyl)-2,2-dimethyl(2H)benzo(h) chromene.

According to the present invention, the fulgimide compound and the chromene compound can be mixed at any ratio depending upon the desired color tone. To obtain such a color tone as grey, brown, amber, etc., it is usually desired that the chromene compound is used in an amount of 0.01 to 10000 parts by weight, preferably, 1 to 1000 parts by weight and, more preferably, 10 to 500 parts by weight per 100 parts by weight of the fulgimide compound. The fulgimide compound and the chromene compound may be added in two or more kinds, respectively.

It is further allowable to blend the photochromic composition with a spiro-oxazine compound to adjust such color tone as grey, brown, amber, etc. Any widely known spiro-oxazine compound can be used without any limitation provided it has a spiro-oxazine skeleton and photochromic property. The spiro-oxazine compounds represented by the following formula (VII) can be preferably used

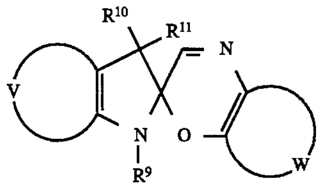

(VII)

wherein $R^9$, $R^{10}$ and $R^{11}$ may be the same or different, and are alkyl groups, cycloalkyl groups, alkoxy groups, alkyleneoxyalkyl groups, alkoxycarbonyl groups, alkoxycarbonylalkyl groups, aryl groups, aralkyl groups, aryloxy groups, alkylenethioalkyl groups, acyl groups, acyloxy groups or amino groups, and $R^{10}$ and $R^{11}$ together may form a ring, $R^9$, $R^{10}$ and $R^{11}$ may have a substituent, respectively, and the substituent may be halogen atom, nitro group, cyano group or heterocyclic group in addition to being the above-mentioned groups.

Moreover, the group

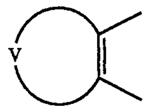

is an aromatic hydrocarbon group or an unsaturated heterocyclic group that may have a substituent, respectively, and the group

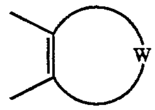

is an aromatic hydrocarbon group or an unsaturated heterocyclic group that may have a substituent, respectively. The substituents may be the same ones as represented by $R^9$, $R^{10}$ and $R^{11}$ above. Among them, a group represented by

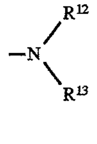

wherein $R^{12}$ and $R^{13}$ are alkyl groups, alkoxy groups or aryl groups that may have a substituent, and $R^{12}$ and $R^{13}$ may be bonded together, cyclized, or may form a nitrogen-containing heterocyclic ring, is preferably used.

Among the spiro-oxazine compounds represented by the above-mentioned formula (VII), it is desired to use those compounds in which $R^9$ is an alkyl group or an alkoxycarbonylalkyl group, $R^{10}$ and $R^{11}$ are cycloalkyls which together are forming a ring,

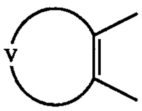

is an aromatic hydrocarbon group which may be partly or entirely substituted with halogen atoms and, particularly, with fluorine, and

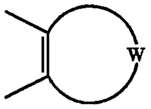

is aromatic hydrocarbon group that may have a substituent and is, particularly, a naphthalene ring substituted with amino group.

Concretely described below are the spiro-oxazine compounds that can be favorably used in the present invention.

Spiro-oxazine compounds:

(1) 1',5'-Dimethyl-6'-fluoro-6"-morpholinodispiro (cyclohexane-1,3'-(3H)indole-2'-(2'H),3"-(3H)naphtho (3,2-a)(1,4)oxazine, (2) 6'-Fluoro-1'-methoxycarbonylethyl-8"-methoxy-6"-piperazinodispiro(cyclohexane-1,3'-(3H)indole-2'-(2H),3"-(3H)naphtho(3,2-a)(1,4)oxazine, (3) 1'-(2-(Dioxazine-2-il)ethyl)-6'-fluoro-6"-(4-methylpiperazino)dispiro(cyclohexane-1,3'-(3H) indole-2'-(2H),3"-(3H)naphtho(3,2-1)(1,4)oxazine, (4) 5',7'-Difluoro-1'-methyl-6"-morpholinodispiro (cyclohexane-1,3'-(3H)indole-2'-(2H),3"-(3H)naphtho (3,2-a)(1,4)oxazine, and (5) 1'-Isobutyl-5'-methyl-6'-fluro-6"-morpholinodispiro (cyclohexane-1,3'-(3H)indole-2'-(2H),3"-(3H)naphtho (2,3-a)(1,4)oxazine.

According to the present invention, the photochromic composition and the spiro-oxazine compound can be mixed at any ratio depending upon the desired color tone. To obtain such a color tone as grey, brown, amber, etc., it is usually desired that the spiro-oxazine compound is used in an amount of 0.01 to 10000 parts by weight, preferably, 0.1 to 1000 parts by weight and, more preferably, 1 to 500 parts by weight per 100 parts by weight of the photochromic composition which comprises a fulgimide compound represented by the above-mentioned formula (I) and the chromene compound. The spiro-oxazine compounds may be added in two or more kinds.

The fulgimide compound of the present invention may be dispersed in an organic solvent to obtain a photochromic fluid that can be used for ornamental applications and the like applications. The fulgimide compound of the present invention may further be dispersed in a polymer such as a thermosetting resin or a thermoplastic resin obtained by polymerizing a polymerizable monomer to obtain molded articles such as photochromic lenses and the like.

In this case, the fulgimide compound represented by the above-mentioned formula (I) or the photochromic composition comprising the fulgimide compound and other photochromic compound such as chromene compound or spiro-oxazine compound, is added in an amount of 0.001 to 20 parts by weight and, preferably, 0.01 to 10 parts by weight per 100 parts by weight of the polymerizable monomer or per 100 parts by weight of the thermoplastic resin.

Any widely known thermosetting resin can be used without any limitation provided it permits a photochromic compound to be uniformly dispersed therein. Examples of the thermosetting resin that can be preferably used include polyhydric acrylic acid and polyhydric methacrylic ester compound such as ethylene glycol diacrylate, diethylene glycol dimethacrylate, triethylene glycol dimethacrylate, tetraethylene glycol dimethacrylate, ethylene glycol bisglycidylmethacrylate, bisphenol A dimethacrylate, 2,2-bis(4-methacryloyloxyethoxyphenyl)propane, and 2,2-bis (3,5-dibromo-4-methacryloyloxyethoxyphenyl)propane; polyhydric allyl compounds such as diallyl phthalate, diallyl terephthalate, diallyl isophthalate, dially tartarate, diallyl epoxysuccinate, diallyl fumarate, diallyl chlorendate, diallyl hexaphthalate, diallyl carbonate, allyl diglycol carbonate and trimethylolpropanetriallyl carbonate; polyhydric thioacrylic acid and polyhydric thiomethacrylic esters such as 1,2-bis(methacryloylthio)ethane, bis(2-acryloylthioethyl) ether, and 1,4-bis(methacryloylthiomethyl)benzene; methacrylate compounds or acrylate compounds such as glycidyl acrylate, glycidyl methacrylate, β-methylglycidyl methacrylate, bisphenol A-monoglycidylether methacrylate, 4-glycidyloxy methacrylate, 3-(glycidyl-2-oxyethoxy)-2-hydroxypropyl methacrylate, 3-(glycidyloxy-1-isopropyloxy)-2-hydroxypropyl acrylate, and 3-(glycidyloxy-2-hydroxypropyloxy)-2-hydroxypropyl acrylate; and a thermosetting resin obtained by polymerizing a radically polymerizable polyfunctional monomer such as divinyl benzene and the like. There can be further exemplified thermosetting resins obtained by copolymerizing the above-mentioned radically polymerizable polyfunctional monomers with radically polymerizable monofunctional monomers like unsaturated carboxylic acids such as acrylic acid, methacrylic acid and maleic anhydride; acrylic and methacrylic ester compounds such as methyl acrylate, methyl methacrylate, benzyl methacrylate, phenyl methacrylate, and 2-hydroxyethyl methacrylate; fumaric ester compounds such as diethyl fumarate and di[henyl fumarate; thioacrylic and thiomethacrylic ester compounds such as methylthioacrylate, benzylthioacrylate and benzylthiomethacrylate; or vinyl compounds such as styrene, chlorostyrene, methylstyrene, vinylnaphthalene, α-methylstyrene dimer and bromostyrene.

There can be further exemplified an addition copolymer of a polyhydric thiol compound such as ethanedithiol, propanetriol, hexanedithiol, pentaerythritol tetrakisthioglycolate or di(2-mercaptoethyl)ether and the above-mentioned radical polymerizable polyfunctional monomer; and a thermoplastic resin obtained by the addition polymerization of a polyhydric isocyanate compound such as diphenylethane diisocyanate, xylylene diisocyanate or p-phenylene diisocyanate and a polyhydric alcohol compound such as ethylene glycol, trimethylolpropane, pentaerythritol or bisphenol A or the above-mentioned thiol compound. These polymerizable monomers can be used in a single kind or being mixed together in two or more kinds.

The photochromic compound can be dispersed in the thermosetting resin in a generally employed method without any limitation. For instance, there can be employed a method wherein the photochromic compound is dissolved in the polymerizable monomer and, then, a polymerization catalyst is added thereto to effect the polymerization with the heat or light to disperse it in the resin, or a method which permits the photochromic compound to stay on the surface of the thermosetting resin.

Furthermore, any thermoplastic resin can be used without any limitation provided it permits the photochromic compound to be uniformly dispersed therein. Optically desired examples thereof include methyl polyacrylate, ethyl polyacrylate, methyl polymethacrylate, ethyl polymethacrylate, polystyrene, polyacrylonitrile, polyvinyl alcohol, polyacrylamide, poly(2-hydroxyethyl methacrylate), polydimethyl siloxane, polycarbonate, etc.

The photochromic compound can be dispersed in the thermoplastic resin by a generally employed method without any limitation. For instance, there can be employed a method in which the thermoplastic resin and the photochromic compound are melted and kneaded at a temperature higher than the melting temperature of the thermoplastic resin.

The composition of the present invention blended with an ultraviolet-ray stabilizer features an improved durability in exhibiting photochromic property. As the ultraviolet-ray stabilizer, any widely known ultraviolet-ray stabilizer added to various plastics can be used without any limitation.

In an attempt to improve durability of the compound of the present invention, a singlet oxygen extinguishing agent and a hindered amine photo stabilizer can be preferably used among various ultraviolet-ray stabilizers.

The fulgimide compounds of the present invention can be used over a wide range of fields as various recording materials, copying materials, potosensitive materials for printing, recording materials for cathode-ray tubes and as photosensitive materials for laser applications to substitute for silver salt photosensitive materials. Moreover, the fulgimide compounds of the present invention can be used as materials for photochromic lenses, for optical filters, as display materials, as actinometers and as ornamental materials.

When the fulgimide compound is used for a photochromic lens, any method can be employed without limitation provided it makes it possible to obtain a uniformdimming property. Concretely speaking, there can be employed a method by which a polymer film in which the fulgimide compound of the present invention is uniformly dispersed is sandwiched at the center of the lens, a method by which the fulgimide compound and a photo initiator are dissolved in a polymerizable monomer by heating, and the polymer is then cured by a predetermined method, and a method by which the fulgimide compound of the present invention is dissolved in, for example, a silicone oil, applied to the lens surfaces at 150° to 200° C. over a period of 10 to 60 minutes, and the surfaces are coated with a curable material to obtain a photochromic lens. It can be further contrived to obtain a photochromic lens by applying the polymer film onto the lens surfaces which are then coated with a curable material.

In the fulgimide compound of the general formula (I) of the present invention in which a particular electron attractive group is directly introduced to the in, de moiety thereof, development of color is favorably suppressed in an initial state of not developing color, and the effect of lengthening the wave is obtained. By using the fulgimide compound which is blended with a chromene compound and a spirooxazine compound, it is allowed to develop such colors as grey, brown, amber as well as a variety of intermediate colors from its no-color state.

Among the fulgimide compounds, furthermore, those in which $R^2$ is a cyano group feature superior durability for reversibly repeating developing of color and extinction of color to that of other fulgimide compounds having a comparable maximum absorption wavelength for developing color.

The invention will now be described in detail by way of Examples to which only, however, the invention is in no way limited.

EXAMPLE 1

10.0 Grams (0.066 mols) of a 3-cyclopropylthienyl ketone and 20.0 g (0.065 mols) of a diethyl 2-adamantylidenesuccinate of the following formula

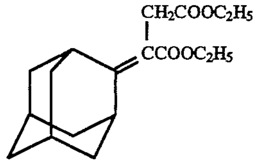

were dissolved in 200 cc of toluene to prepare a solution. This toluene solution was added to a solution of 200 cc of toluene in which 5.6 g of sodium hydride was dispersed, and the mixture solution was vigorously stirred maintaining a temperature of not higher than 0° C. for 10 hours. The solution was hydrolyzed with an excess of 10% alcoholic potassium hydroxide solution. Then, a dicarboxylic acid obtained by the acidification with hydrochloric acid was treated with 100 cc of acetyl chloride and was purified by chromatography on silica gel to obtain 11.5 g of a fulgide compound of the following formula,

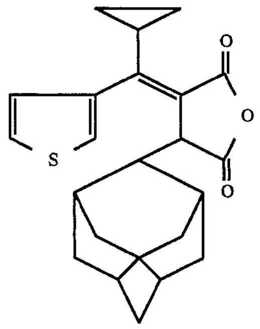

The obtained compound was dissolved in 100 cc of acetone, and to which was dropwisely added 5.5 g (0.131 mols) of cyanamide, followed by stirring for two hours. After the reaction, the solvent was removed, and the reaction product was dissolved in acetyl chloride and was refluxed for one hour to cyclize it. The obtained compound was refluxed in an O-dichlorobenzene for one hour to rearrange it into a fulgimide compound (1) mentioned below. By using chloroform and hexane as eluents, this compound was purified by chromatography on the silica gel, and was recrystallized from toluene and isopropyl alcohol in the form of pale-yellow needle crystals maintaining a yield of 15%. The elemental analysis of this compound was C 70.79%, H 5.72%, N 7.15%, O 8.20%, S 8.23%, which was in very good agreement with C 70.74%, H 5.68%, N 7.17%, O 8.19%, S 8.21% that was calculated from $C_{23}H_{22}N_2O_2S$.

Measurement of a proton nuclear magnetic resonance spectrum indicated a peak 2H near δ7.0 to 7.5 ppm due to proton of a thiophene ring, a peak 1H near δ3.7 ppm due to proton that is 1.5-shift, and a peak 19H of protons near δ1.3 to 2.5 ppm due to a cyclopropyl group and a 2-adamantylidene group.

Furthermore, measurement of a $^{13}C$-nuclear magnetic resonance spectrum ($^{13}C$-NMR) indicated a peak near δ27 to 70 ppm due to carbon of the 2-adamantylidene group, a peak near δ10.2 ppm due to carbon of the cyclopropyl group, a peak near δ110 to 160 ppm due to carbon of the thiophene ring, and a peak near δ160 to 170 ppm due to carbon of a bond >C=O.

From the above results, it was confirmed that the product that was isolated was a gulgimide compound (1) represented by the following structural formula, (1)

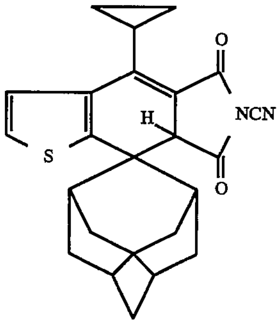

EXAMPLE 2

A fulgimide compound of the following structural formula was obtained in the same procedure as in Example 1 but using $NH_3$ instead of the cyanamide of Example 1.

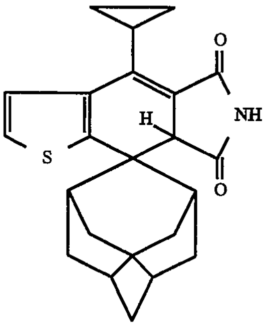

6.5 Grams (0.015 mols) of this compound was dissolved in tetrahydrofurane, with which metal potassium was reacted at room temperature to obtain 5.4 g of imidopotassium of the following formula,

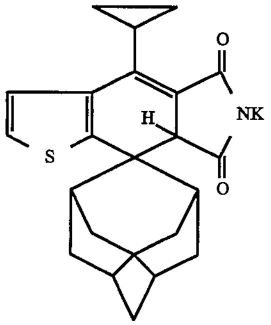

By reacting this compound with 0.79 grams (0.01 mols) of acetyl chloride in dimethylformamide, the following fulgimide compound (2) was obtained. By using chloroform and hexane as eluents, this compound was purified by chromatography on silica gel, and was recrystallized from toluene and isopropyl alcohol in the form of yellow needle crystals maintaining a yield of 42%. The elemental analysis of this compound was C 71.61%, H 6.02%, N 3.36%, O 11.47%, S 7.70%, which was in very good agreement with C 71.57%, H 6.01%, N 3.34%, O 11.44%, S 7.64% that was calculated from $C_{25}H_{25}NO_3S$.

Measurement of a proton nuclear magnetic resonance spectrum indicated a peak 2H near δ7.0 to 8.0 ppm due to aromatic proton, a peak 1H near δ3.7 ppm due to proton that is 1-5 shift, and a peak 22H near δ1.0 to 2.2 ppm due to a cyclopropyl group and a 2-adamantylidene group.

Furthermore, measurement of a $^{13}C$-nuclear magnetic resonance spectrum ($^{13}C$-NMR) indicated a peak near δ27 to 52 ppm due to carbon of the 2-adamantylidene group, a peak near δ9.7 ppm due to carbon of the cyclopropyl group, a peak near δ25 to 35 ppm due to carbon of the acetyl group or methyl group, a peak near δ110 to 160 ppm due to carbon of a thiophene ring and a peak near δ160 to 170 ppm due to carbon of a bond >C=O.

From the above results, it was confirmed that the product that was isolated was a fulgimide compound (2) represented by the following structural formula, (2)

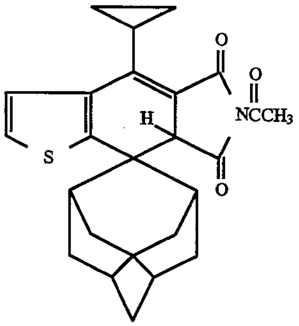

EXAMPLE 3

3.3 Grams (0.01 mols) of a fulgimide compound of the following formula,

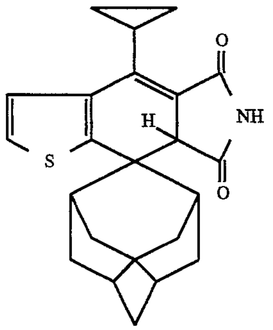

was dissolved in a tetrahydrofuran and was reacted with 1 g of metal potassium at room temperature to obtain 3.0 g of imidopotassium of the following formula,

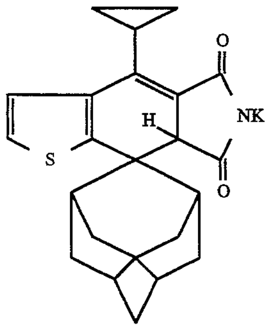

This compound was reacted with 1.41 g (0.01 mols) of benzoyl chloride in dimethylformamide to obtain the following fulgimide compound (3). By using chloroform and hexane as eluents, this compound was purified by chromatography on silica gel, and was recrystallized from toluene and isopropyl alcohol in the form of pale-yellowish crystals maintaining a yield of 55%. The elemental analysis of this compound was C 72.40%, H 5.88%, N 3.27%, O 7.15%, S 7.45%, which was in very good agreement with C 72.36%, H 5.84%, N 3.25%, O 11.12%, S 7.43% that was calculated from $C_{26}H_{25}NO_3S$.

Measurement of a proton nuclear magnetic resonance spectrum indicated a peak 7H near δ7.0 to 7.5 ppm due to proton of a thiophene ring and a benzene ring, a peak 1H near δ3.7 ppm due to proton that is 1-5 shifted, and a peak 19H near δ1.3 to 2.5 ppm due to protons of a cyclopropyl group and a 2-adamantylidene group.

Furthermore, measurement of a $^{13}C$-nuclear magnetic resonance spectrum ($^{13}C$-NMR) indicated a peak near δ27 to 70 ppm due to carbon of the 2-adamantylidene group, a peak near δ10.2 ppm due to carbon of the cyclopropyl group, a peak near δ110 to 160 ppm due to carbon of a thiophene ring and benzene ring, and a peak near δ160 to 170 ppm due to carbon of a bond >C=O.

From the above results, it was confirmed that the product that was isolated was a fulgimide compound (3) represented by the following structural formula, (3)

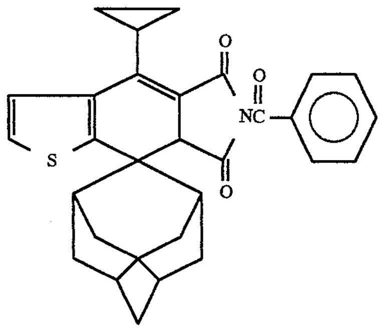

EXAMPLES 4 to 33

A variety of fulgimide compounds were synthesized using starting materials shown in Table 1 in the same procedure as in Examples 1 to 3.

The obtained compounds were subjected to the elemental analysis and were measured for their proton nuclear magnetic resonance spectrum and $^{13}C$-nuclear magnetic resonance spectrum in the same procedure as in Examples 1 to 3. It was confirmed that the compounds were those represented by the structural formulas (4) to (33) shown in Table 1. Table 2 shows elemental analyses of these compounds, values calculated from the structural formulas of the compounds, and characteristic proton nuclear magnetic resonance spectra.

TABLE 1
| Compound No. | Starting materials | | Products | Yields |
|---|---|---|---|---|
| 4 | 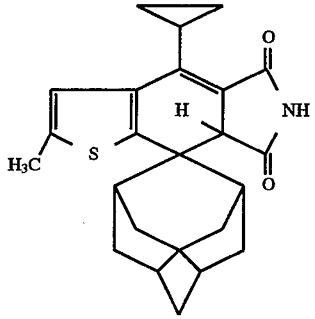 | 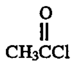 | 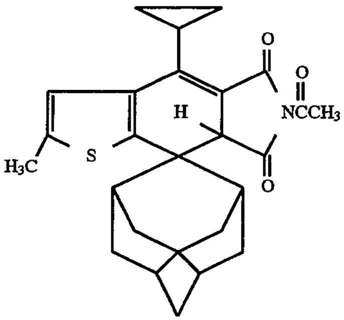 | 35 |
| 5 | 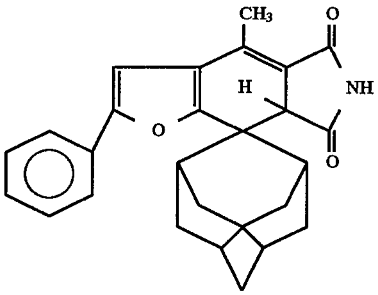 | BrCN | 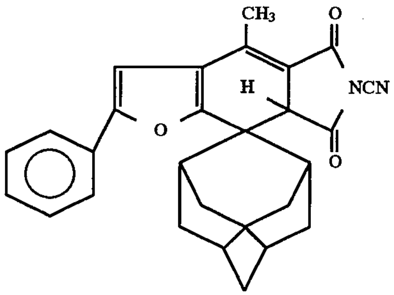 | 25 |
| 6 | 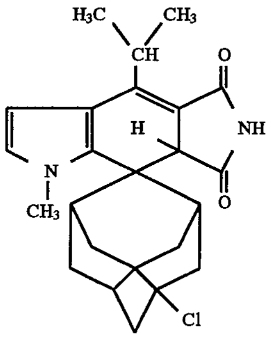 | $ClSO_2CH_3$ | 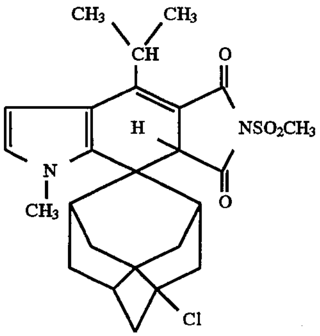 | 29 |

TABLE 1-continued
| Compound No. | Starting materials | | Products | Yields |
|---|---|---|---|---|
| 7 | 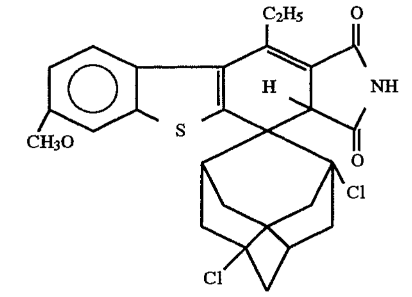 | 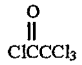 | 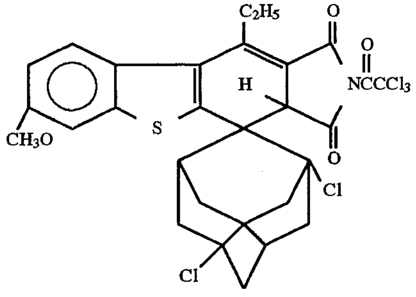 | 15 |
| 8 | 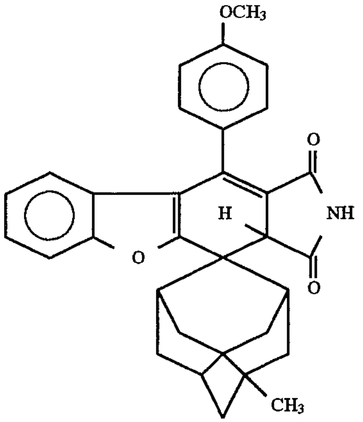 | 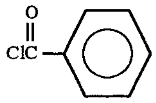 | 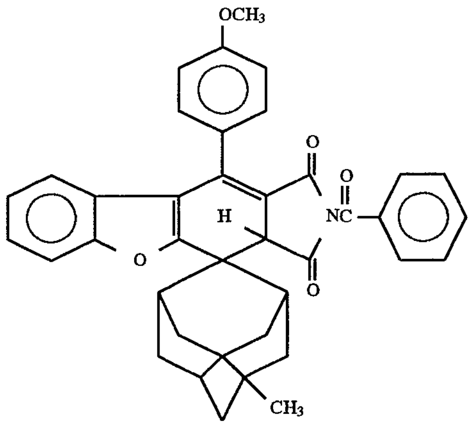 | 27 |
| 9 | 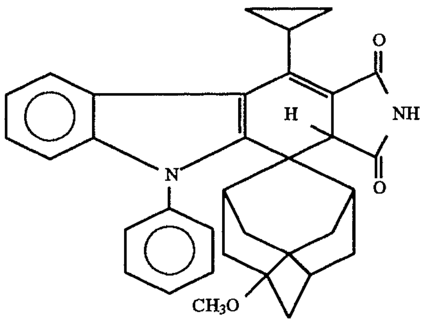 | $BrCCl_3$ | 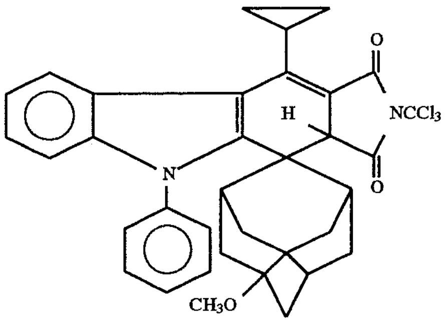 | 22 |

TABLE 1-continued
| Compound No. | Starting materials | | Products | Yields |
|---|---|---|---|---|
| 10 | 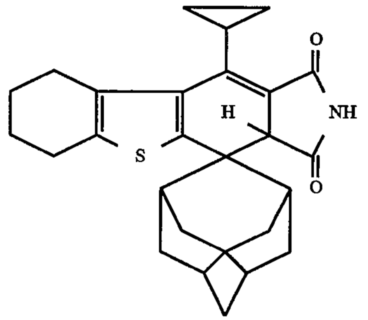 | 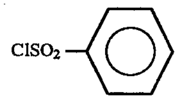 | 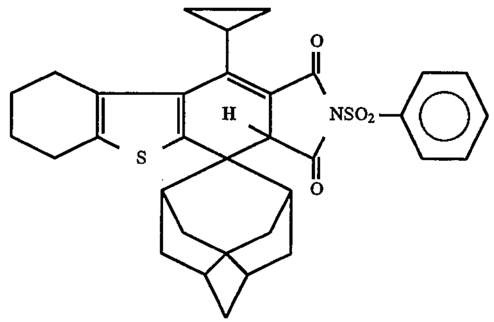 | 17 |
| 11 | 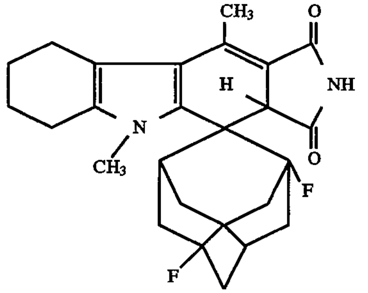 | 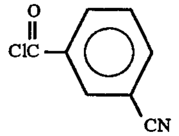 | 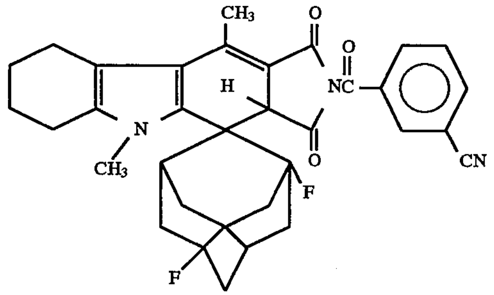 | 25 |
| 12 | 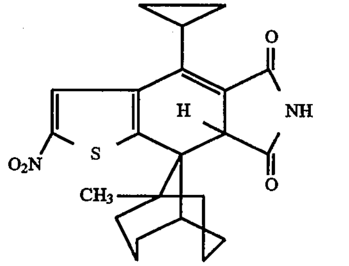 | 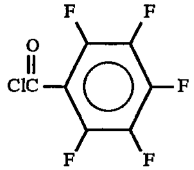 | 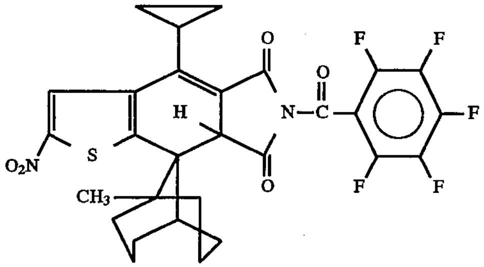 | 30 |

TABLE 1-continued
| Compound No. | Starting materials | | Products | Yields |
|---|---|---|---|---|
| 13 | 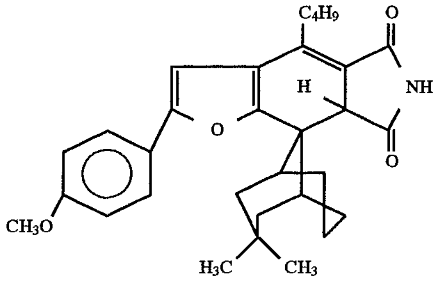 | 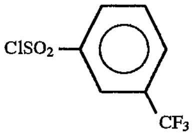 | 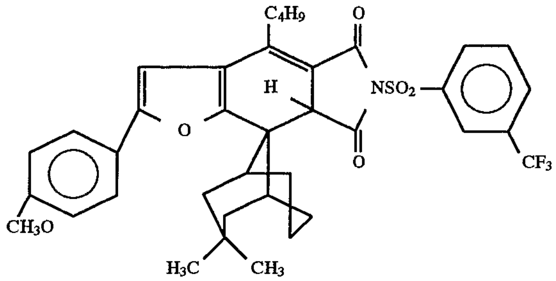 | 18 |
| 14 | 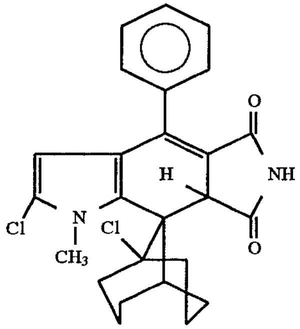 | $CF_3I$ | 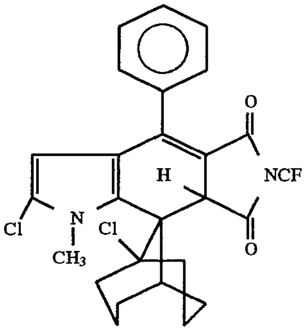 | 27 |
| 15 | 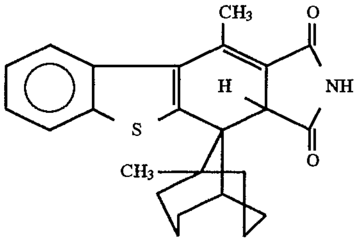 | $Cl\overset{O}{\overset{\|}{C}}OC_2H_5$ | 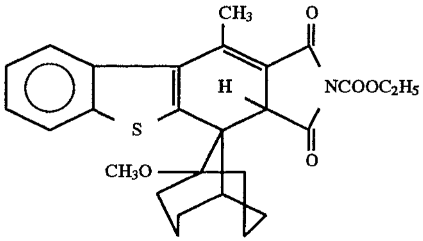 | 30 |

TABLE 1-continued
| Compound No. | Starting materials | | Products | Yields |
|---|---|---|---|---|
| 16 | 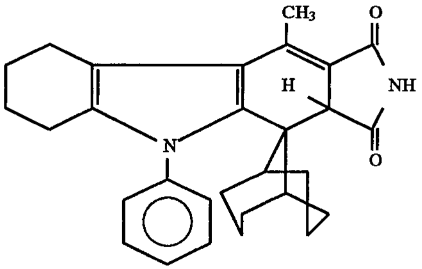 | 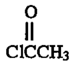 | 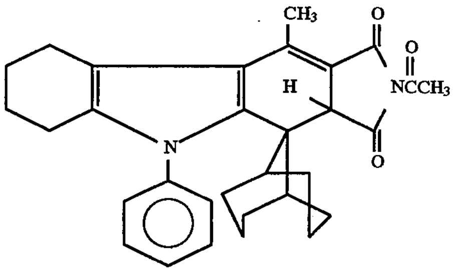 | 33 |
| 17 | 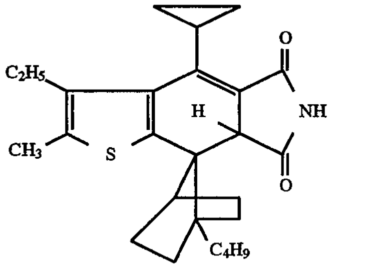 | 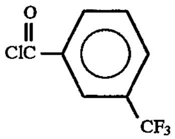 | 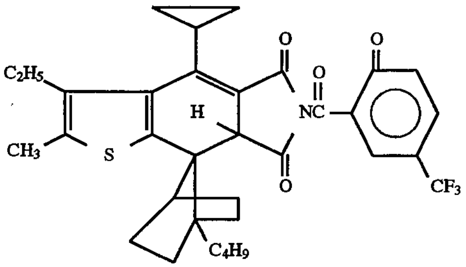 | 27 |
| 18 | 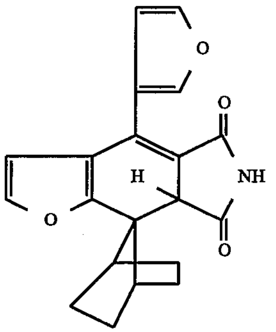 | BrCN | 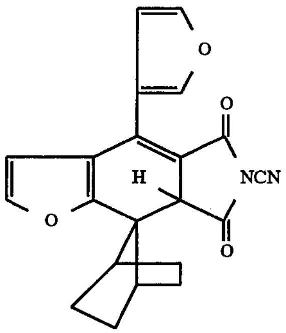 | 15 |

TABLE 1-continued
| Compound No. | Starting materials | | Products | Yields |
|---|---|---|---|---|
| 19 | 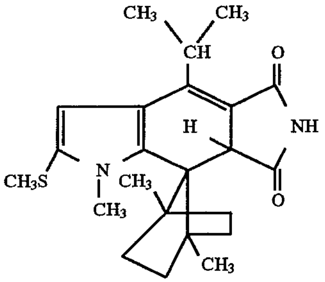 | $CF_3I$ | 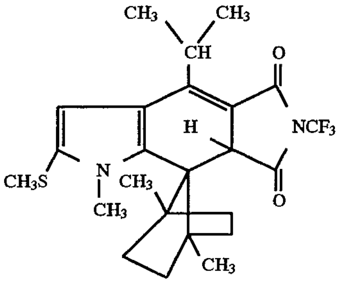 | 15 |
| 20 | 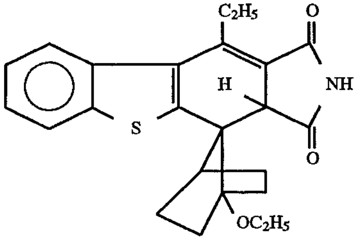 | $ClSO_2C_2H_5$ | 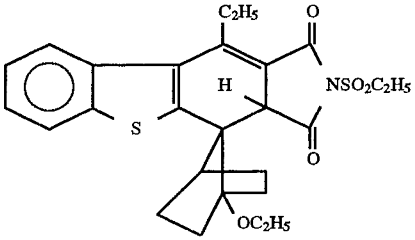 | 13 |
| 21 | 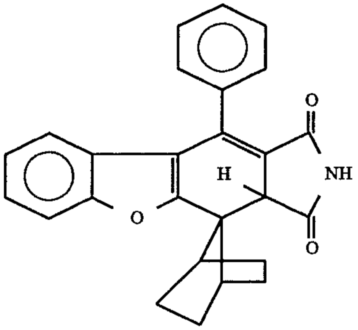 | $BrCCl_3$ | 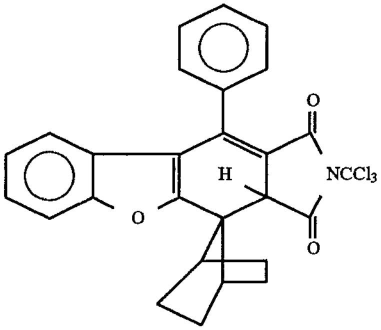 | 20 |

TABLE 1-continued
| Compound No. | Starting materials | | Products | Yields |
|---|---|---|---|---|
| 22 | 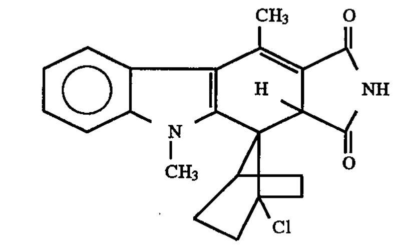 | 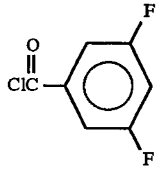 | 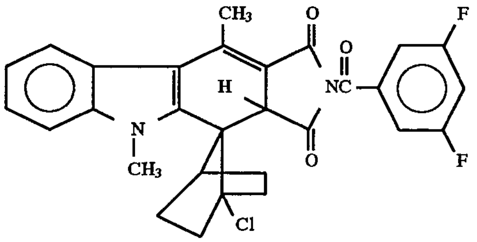 | 22 |
| 23 | 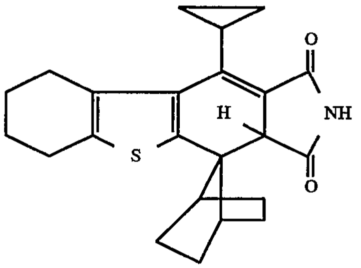 | 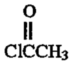 | 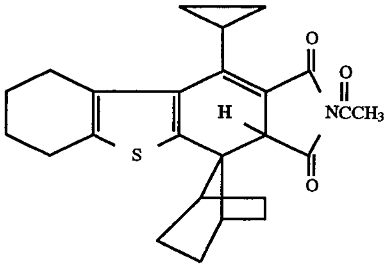 | 25 |
| 24 | 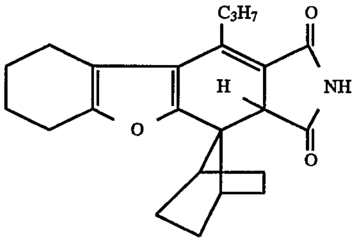 | BrCCl$_3$ | 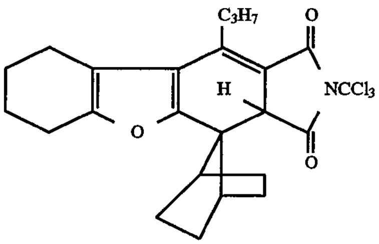 | 18 |
| 25 | 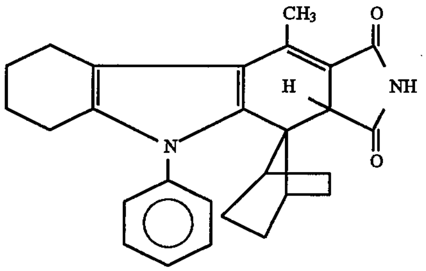 | 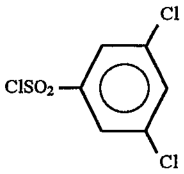 | 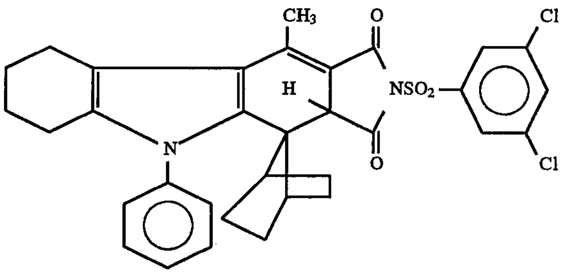 | 22 |

TABLE 1-continued
| Compound No. | Starting materials | | Products | Yields |
|---|---|---|---|---|
| 26 | 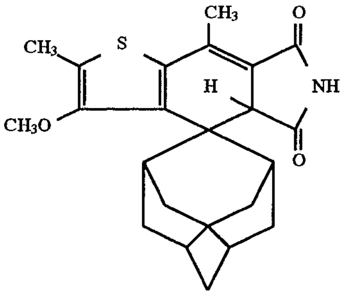 | 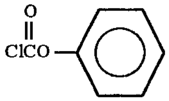 | 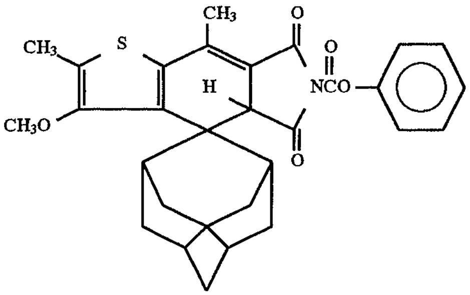 | 30 |
| 27 | 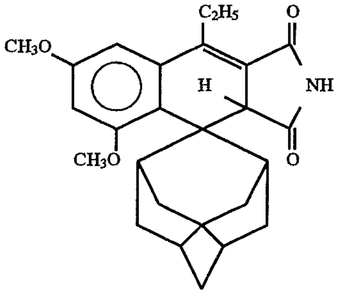 | $ClSO_3H$ | 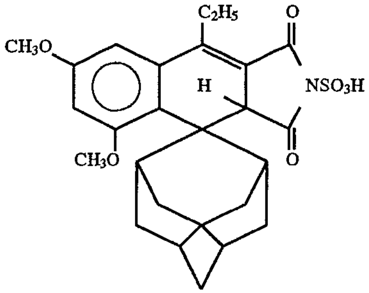 | 25 |
| 28 | 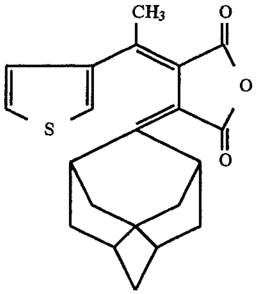 | $H_2NCN$ | 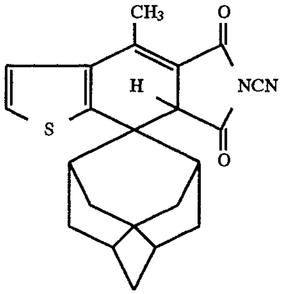 | 32 |

TABLE 1-continued
| Compound No. | Starting materials | | Products | Yields |
|---|---|---|---|---|
| 29 | 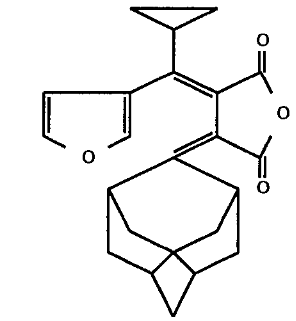 | $H_2NCN$ | 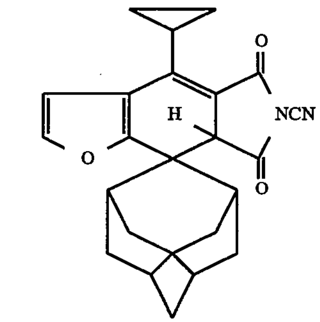 | 25 |
| 30 | 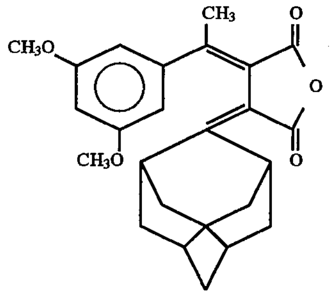 | $H_2NCN$ | 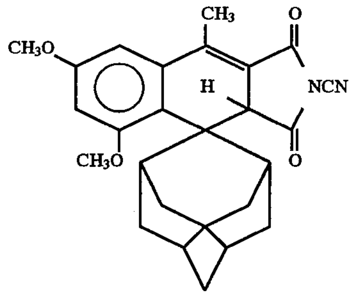 | 33 |
| 31 | 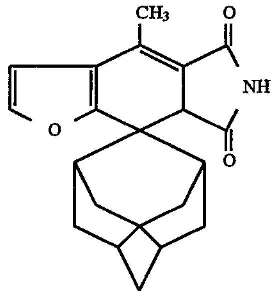 | BrCN | 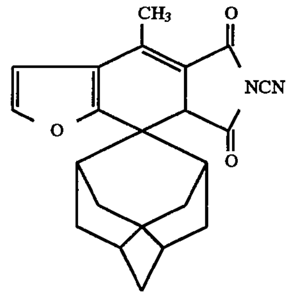 | 20 |

TABLE 1-continued
| Compound No. | Starting materials | | Products | Yields |
| --- | --- | --- | --- | --- |
| 32 | 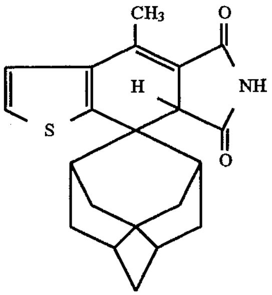 | $CH_3\overset{O}{\overset{\parallel}{C}}Cl$ | 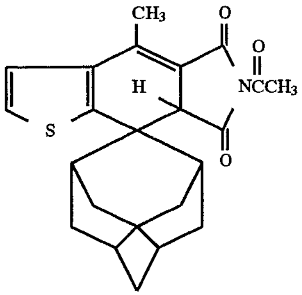 | 30 |
| 33 | 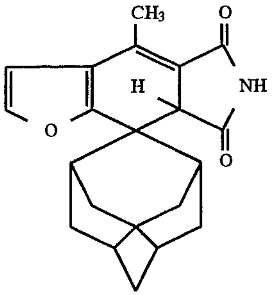 | 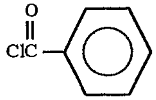 | 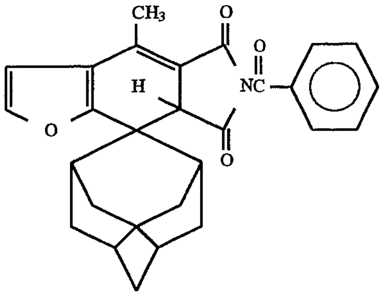 | 30 |

TABLE 2

| Compound No. | Elemental analysis (%) Found C | H | N | O | S | other | Calculated C | H | N | O | S | other | $^1$H-NMR spectra (ppm) |
|---|---|---|---|---|---|---|---|---|---|---|---|---|---|
| 4 | 71.31 | 6.52 | 3.37 | 11.45 | 7.63 | | 71.23 | 6.46 | 3.32 | 11.39 | 7.61 | | δ7.2:1H, δ3.7:1H, δ1.3~2.5:25H |
| 5 | 76.50 | 5.75 | 6.63 | 11.35 | | | 76.40 | 5.70 | 6.60 | 11.31 | | | δ6.4~7.5:6H, δ3.6:1H, δ1.5~2.5:17H |
| 6 | 62.15 | 6.37 | 3.05 | 13.82 | 6.95 | Cl 7.90 | 62.12 | 6.30 | 3.02 | 13.79 | 6.91 | Cl 7.86 | δ6.2~7.5:2H, δ3.7:1H, δ1.5~2.7:26H |
| 7 | 51.25 | 3.91 | 2.17 | 10.02 | 4.95 | Cl 27.92 | 51.44 | 3.85 | 2.14 | 9.99 | 4.90 | Cl 27.88 | δ7.2~7.6:3H, δ3.4~3.7:4H, δ1.5~2.5:18H |
| 8 | 78.26 | 5.72 | 2.46 | 13.75 | | | 78.20 | 5.70 | 2.40 | 13.71 | | | δ7.0~7.5:13H, δ3.4~3.7:4H, δ1.2~2.7:16H |
| 9 | 66.87 | 5.15 | 2.32 | 7.89 | | Cl 17.95 | 66.84 | 5.11 | 2.29 | 7.86 | | Cl 17.90 | δ7.2~7.6:9H, δ3.4~3.7:4H, δ1.2~2.7:18H |
| 10 | 68.70 | 5.96 | 2.55 | 11.45 | 11.49 | | 68.67 | 5.94 | 2.50 | 11.43 | 11.46 | | δ7.0~7.5:5H, δ3.7:1H, δ1.2~2.7:27H |
| 11 | 71.37 | 5.65 | 7.61 | 8.70 | | F 6.85 | 71.34 | 5.62 | 7.56 | 8.64 | | F 6.84 | δ7.0~7.5:4H, δ3.8:1H, δ1.2~2.7:26H |
| 12 | 57.45 | 3.87 | 4.63 | 13.22 | 5.33 | F 15.72 | 57.42 | 3.82 | 4.62 | 13.19 | 5.29 | F 15.66 | δ7.2:1H, δ3.7:1H, δ1.2~2.7:21H |
| 13 | 67.17 | 5.96 | 2.11 | 11.79 | 4.75 | F 8.41 | 67.14 | 5.93 | 2.06 | 11.77 | 4.72 | F 8.38 | δ7.0~7.7:9H, δ3.4~3.8:4H, δ1.2~2.7:27H |
| 14 | 61.12 | 4.58 | 2.77 | 6.31 | | F 11.18<br>Cl 14.31 | 61.07 | 4.53 | 2.74 | 6.26 | | F 11.15<br>Cl 14.26 | δ6.4~7.5:6H, δ3.7:1H, δ1.2~2.7:16H |
| 15 | 67.65 | 6.13 | 2.97 | 16.73 | 6.75 | | 67.62 | 6.09 | 2.92 | 16.68 | 6.68 | | δ7.2~7.6:4H, δ3.4~3.8;4H, δ1.2~2.7:21H |
| 16 | 78.01 | 6.15 | 5.91 | 10.07 | | | 77.96 | 6.12 | 5.87 | 10.05 | | | δ7.0~7.5;5H, δ3.7:1H, δ1.2~2.7:23H |
| 17 | 68.59 | 6.13 | 2.38 | 8.11 | 5.43 | F 9.60 | 68.55 | 6.09 | 2.35 | 8.06 | 5.38 | F 9.57 | δ7.0~7.5:4H, δ3.7:1H, δ1.2~2.7:31H |
| 18 | 69.85 | 4.79 | 7.81 | 17.75 | | | 69.80 | 4.74 | 7.75 | 17.71 | | | δ6.2~7.0:5H, δ3.7:1H, δ1.2~2.7:11H |
| 19 | 61.83 | 6.31 | 6.05 | 6.91 | 6.95 | F 12.25 | 61.78 | 6.26 | 6.00 | 6.86 | 6.87 | F 12.22 | δ6.3:1H, δ3.8:1H, δ1.2~2.7:27H |
| 20 | 62.55 | 5.91 | 2.83 | 16.05 | 12.85 | | 62.50 | 5.85 | 2.80 | 16.01 | 12.83 | | δ7.0~7.5:4H, δ3.71H, δ1.2~2.7:24H |
| 21 | 62.91 | 3.95 | 2.75 | 9.35 | | Cl 21.25 | 62.87 | 3.91 | 2.72 | 9.31 | | Cl 21.20 | δ7.0~7.5:9H:3.7:1H, δ1.2~2.7:10H |
| 22 | 68.35 | 4.96 | 2.82 | 9.47 | | F 7.51<br>Cl 7.21 | 68.30 | 4.94 | 2.75 | 9.41 | | F 7.45<br>Cl 7.15 | δ7.0~7.6:7H, δ3.7:1H, δ1.2~2.7:17H |
| 23 | 71.25 | 6.51 | 3.35 | 11.41 | 7.65 | | 71.23 | 6.46 | 3.32 | 11.39 | 7.61 | | δ3.7:1H, δ1.2~2.7:26H |
| 24 | 59.35 | 5.41 | 2.90 | 9.93 | | Cl 22.55 | 59.33 | 5.39 | 2.88 | 9.88 | | Cl 22.51 | δ3.6:1H, δ1.2~2.7:25H |
| 25 | 63.61 | 4.91 | 4.55 | 10.31 | 5.20 | Cl 11.73 | 63.56 | 4.85 | 4.49 | 10.26 | 5.14 | Cl 11.69 | δ7.0~7.6:8H, δ3.7:1H, δ1.2~2.7:21H |
| 26 | 69.21 | 5.85 | 2.83 | 15.91 | 6.40 | | 69.16 | 5.80 | 2.78 | 15.89 | 6.37 | | δ7.0~7.6:5H, δ3.2~3.8:4H, δ1.2~2.7:20H |
| 27 | 65.95 | 6.45 | 3.11 | 24.61 | | | 65.92 | 6.42 | 3.07 | 24.59 | | | δ7.2~7.5:2H, δ3.4~3.8:7H, δ1.2~2.7:20H |
| 28 | 69.24 | 5.55 | 7.71 | 8.80 | 8.85 | | 69.21 | 5.53 | 7.69 | 8.78 | 8.80 | | δ7.0~7.5:2H, δ3.8:1H, δ1.2~2.7:17H |

EXAMPLES 34 to 66

0.04 Parts of fulgimide compounds shown in Table 3, 70 parts of tetraethyleneglycol dimethacrylate, 15 parts of triethyleneglycol dimethacrylate, 10 parts of glycidyl methacrylate, 5 parts of 2-hydroethyl methacrylate and 1 part of perbutyl ND as a polymerization catalyst, were sufficiently mixed together until they were completely dissolved. The mixture solution was poured into a mold constituted by a glass plate and a gasket of an ethylene/vinyl acetate copolymer, and its temperature was elevated in an air oven from 35° C. to 90° C. over a period of 20 hours to effect the polymerization. After the polymerization, the polymer was taken out from the glass mold.

The obtained polymer plate was irradiated with xenon light by using a Xenon Long-Life Fade Meter FAL-25AX-HC (output: 2.5 KW, source of light: xenon long-life arc lamp) manufactured by Suga Shikenki Co., in order to measure a maximum absorption wavelength in a state of developing color. The initial color tone was observed by eyes, and YI of the samples was measured by using a color-difference meter (Model SM-4) manufactured by Suga Shikenki Co. The wear life (T½) was also measured in compliance with JIS L0843 and JIS B7754. T½ is defined to be the time until the color density decreases down to one-half the initial value when the polymer plate is irradiated with light by using the fade meter.

For the purpose of comparison, the fulgimide compounds represented by the following formulas (A) to (I) were also used to prepare polymer plates to measure their properties in the same procedure as described above.

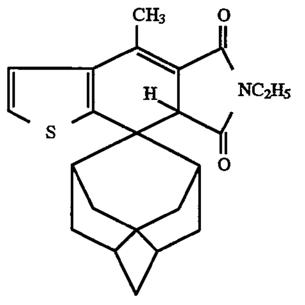

(A)

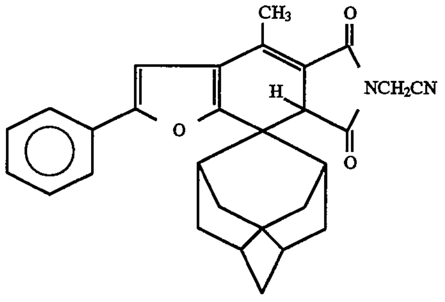

(B)

-continued

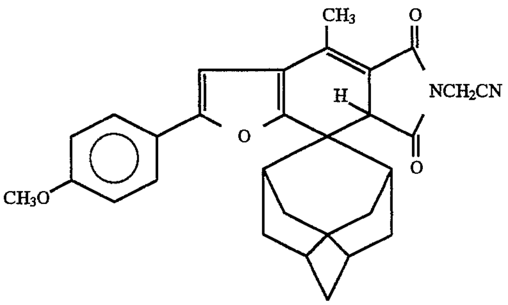

(C)

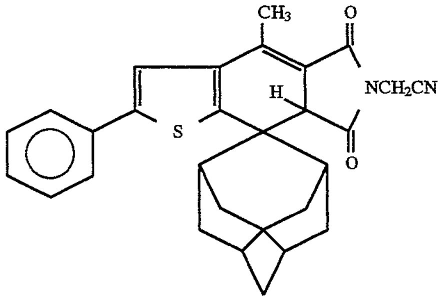

(D)

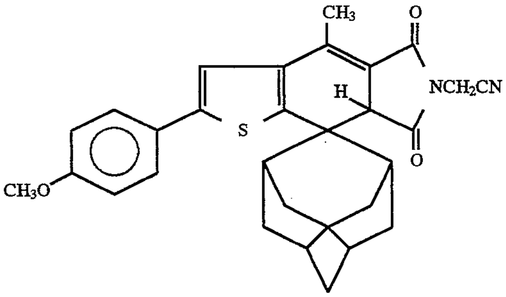

(E)

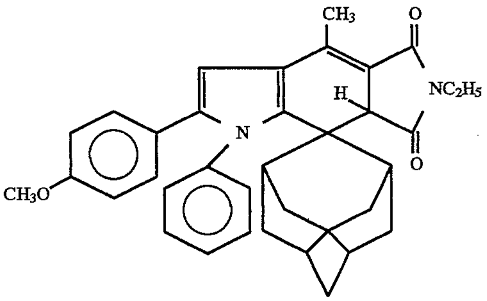

(F)

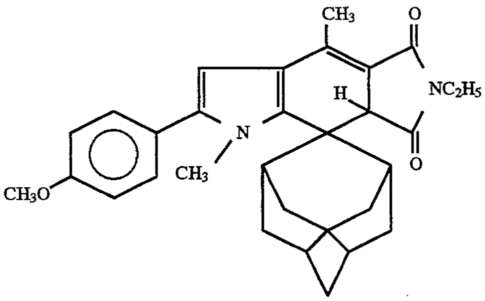

(G)

-continued

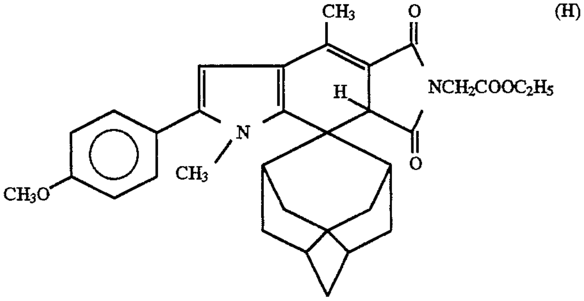

(H)

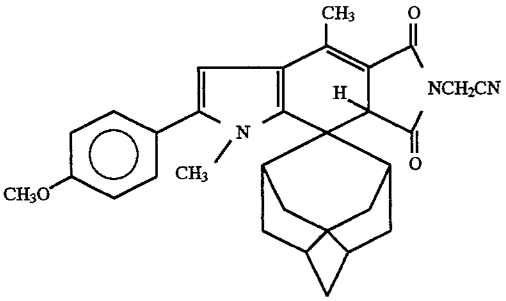

(I)

TABLE 3

| Sample No. | Compound No. | Color density | λ max (nm) | Initial color Visually observed | YI | T½ (hour) |
|---|---|---|---|---|---|---|
| (Example) | | | | | | |
| 34 | (1) | 0.65 | 615 | colorless | 1.85 | 400 |
| 35 | (2) | 1.20 | 560 | colorless | 2.01 | 140 |
| 36 | (3) | 0.90 | 570 | colorless | 3.84 | 135 |
| 37 | (4) | 1.43 | 562 | colorless | 2.15 | 140 |
| 38 | (5) | 1.12 | 603 | colorless | 3.96 | 260 |
| 39 | (6) | 0.95 | 601 | pale yellow | 4.85 | 110 |
| 40 | (7) | 0.85 | 550 | colorless | 2.15 | 100 |
| 41 | (8) | 0.98 | 541 | colorless | 3.94 | 110 |
| 42 | (9) | 1.02 | 610 | colorless | 3.85 | 145 |
| 43 | (10) | 1.12 | 620 | pale yellow | 4.99 | 140 |
| 44 | (11) | 0.88 | 630 | colorless | 2.35 | 100 |
| 45 | (12) | 1.02 | 593 | colorless | 2.25 | 140 |
| 46 | (13) | 0.89 | 595 | pale yellow | 4.78 | 110 |
| 47 | (14) | 0.75 | 603 | pale yellow | 4.89 | 100 |
| 48 | (15) | 0.85 | 520 | colorless | 2.95 | 110 |
| 49 | (16) | 1.05 | 625 | colorless | 3.56 | 100 |
| 50 | (17) | 1.10 | 610 | colorless | 3.10 | 140 |
| 51 | (18) | 1.11 | 613 | colorless | 2.95 | 250 |
| 52 | (19) | 0.81 | 603 | colorless | 3.05 | 110 |
| 53 | (20) | 0.95 | 548 | pale yellow | 4.85 | 100 |
| 54 | (21) | 0.95 | 540 | colorless | 2.95 | 115 |
| 55 | (22) | 0.77 | 612 | colorless | 3.26 | 110 |
| 56 | (23) | 0.87 | 600 | colorless | 2.36 | 140 |
| 57 | (24) | 0.94 | 576 | colorless | 2.45 | 140 |
| 58 | (25) | 0.71 | 619 | colorless | 3.26 | 100 |
| 59 | (26) | 0.54 | 546 | colorless | 3.84 | 120 |
| 60 | (27) | 0.68 | 568 | pale yellow | 4.68 | 100 |
| 61 | (28) | 0.56 | 604 | colorless | 2.06 | 270 |
| 62 | (29) | 0.98 | 600 | colorless | 2.01 | 385 |
| 63 | (30) | 0.73 | 590 | colorless | 2.21 | 210 |
| 64 | (31) | 0.65 | 580 | colorless | 2.00 | 265 |
| 65 | (32) | 0.70 | 550 | colorless | 2.11 | 105 |
| 66 | (33) | 0.58 | 550 | colorless | 2.16 | 100 |
| (Comparative Example) | | | | | | |
| 1 | A | 0.68 | 540 | yellow | 10.03 | 100 |
| 2 | B | 0.75 | 550 | yellow | 10.65 | 95 |
| 3 | C | 0.77 | 560 | yellow | 17.56 | 95 |
| 4 | D | 0.82 | 570 | yellow | 10.75 | 90 |

TABLE 3-continued

| Sample No. | Compound No. | Color density | λ max (nm) | Initial color Visually observed | Initial color YI | T½ (hour) |
|---|---|---|---|---|---|---|
| 5 | E | 0.90 | 580 | yellow | 18.21 | 90 |
| 6 | F | 0.75 | 600 | yellow | 19.23 | 80 |
| 7 | G | 0.88 | 610 | yellow | 19.56 | 85 |
| 8 | H | 0.78 | 620 | yellow | 19.52 | 80 |
| 9 | I | 0.73 | 630 | yellow | 18.89 | 80 |

EXAMPLES 67 to 93

Photochromic polymer plates were prepared in the same procedure as in Example 5 but by using fulgimide compounds and chromene compounds shown in Table 4 in amounts shown in Table 4 instead of using fulgimide compounds of Examples 34 to 66.

The obtained polymer plates were irradiated with the sun light for 10 minutes and color tone at that moment was observed by eyes. The samples were also measured for their YI by using the color-difference meter (Model SM-4) manufactured by Suga Shikenki Co. The results were as shown in Table 4.

The following chromene compounds were used.

TABLE 4

| | Fulgimide compound No. | Amount of fulgimide (parts) | Chromene compound No. | Amount of chromene compound (parts) | Initial color Color tone | Initial color YI-value | Color tone after irradiated with sun light for 10 min. |
|---|---|---|---|---|---|---|---|
| Example No. | | | | | | | |
| 67 | 29 | 0.1 | 2 | 0.05 | colorless | 2.36 | grey |
| 68 | 29 | 0.1 | 2 | 0.1 | colorless | 2.62 | brown |
| 69 | 29 | 0.1 | 2 | 0.2 | colorless | 2.85 | light brown |
| 70 | 29 | 0.2 | 2 | 0.1 | colorless | 2.98 | grey |
| 71 | 29 | 0.5 | 2 | 0.5 | colorless | 3.74 | brown |
| 72 | 29 | 1.0 | 2 | 1.0 | pale yellow | 4.31 | brown |
| 73 | 29 | 0.05 | 2 | 0.05 | colorless | 2.14 | brown |
| 74 | 29 | 0.02 | 2 | 0.01 | colorless | 1.84 | light grey |
| 75 | 1 | 0.1 | 2 | 0.75 | colorless | 2.22 | grey |
| 76 | 2 | 0.1 | 1 | 0.1 | colorless | 2.34 | light brown |
| 77 | 3 | 0.1 | 1 | 0.05 | pale yellow | 4.56 | amber |
| 78 | 5 | 0.1 | 1 | 0.05 | pale yellow | 4.75 | green |
| 79 | 6 | 0.1 | 3 | 0.3 | pale yellow | 5.88 | light brown |
| 80 | 7 | 0.1 | 4 | 0.5 | colorless | 2.58 | light brown |
| 81 | 10 | 0.1 | 1 | 0.1 | pale yellow | 5.98 | green |
| 82 | 12 | 0.1 | 5 | 0.08 | colorless | 2.70 | grey |
| 83 | 13 | 0.1 | 2 | 0.1 | pale yellow | 5.74 | brown |
| 84 | 14 | 0.1 | 5 | 0.2 | pale yellow | 5.87 | light brown |
| 85 | 18 | 0.1 | 2 | 0.1 | colorless | 3.54 | grey |
| 86 | 24 | 0.1 | 1 | 0.05 | colorless | 2.94 | grey |
| 87 | 26 | 0.1 | 3 | 0.4 | pale yellow | 4.61 | maroon brown |
| 88 | 28 | 0.1 | 2 | 0.02 | colorless | 2.47 | grey |
| 89 | 30 | 0.1 | 4 | 0.1 | colorless | 2.65 | light grey |
| 90 | 31 | 0.1 | 1 | 0.05 | colorless | 2.45 | grey |
| 91 | 29 | 0.1 | 1/2 | 0.02/0.03 | colorless | 2.42 | grey |
| 92 | 31 | 0.1 | 1/2 | 0.07/0.03 | colorless | 2.56 | amber |
| 93 | 1/2 | 0.05/0.05 | 1 | 0.08 | colorless | 2.61 | brown |
| Comparative Example No. | | | | | | | |
| 10 | A | 0.1 | 1 | 0.05 | yellow | 12.56 | maroon brown |
| 11 | C | 0.1 | 1 | 0.05 | yellow | 21.07 | maroon brown |
| 12 | E | 0.1 | 1 | 0.05 | yellow | 21.85 | grey |
| 13 | G | 0.1 | 1 | 0.05 | yellow | 22.68 | green |
| 14 | I | 0.1 | 2 | 0.05 | yellow | 23.45 | grey |

(1)

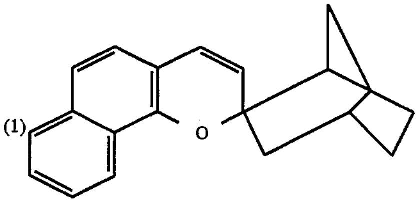

TABLE 4-continued

| Fulgimide compound | Amount of fulgimide | Chromene compound | Amount of chromene compound | Initial color | | Color tone after irradiated with sun light for |
|---|---|---|---|---|---|---|
| No. | (parts) | No. | (parts) | Color tone | YI-value | 10 min. |

(2) 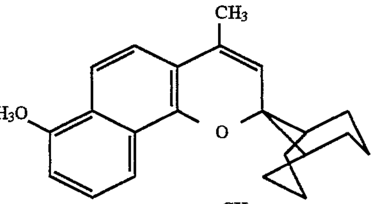

(3) 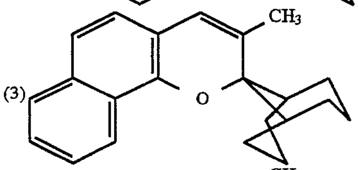

(4) 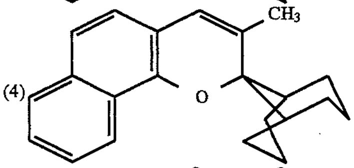

(5) 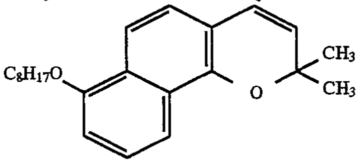

EXAMPLES 94 to 110

Photochromic polymer plates were prepared in the same procedure as in Examples 67 to 93 but by using fulgimide compounds, chromene compounds and spiro-oxazine compounds shown in Table 5 in amounts shown in Table 5 instead of using fulgimide compounds and chromene compounds of Examples 67 to 93, in order to measure their properties.

The following spiro-oxazine were used.

TABLE 5

| Sample No. | Fulgimide compound No. | Amount of fulgimide (parts) | Chromene compound No. | Amount of chromene compound (parts) | Spiro-oxazine compound No. | Amount of spiro-oxazine compound (parts) | Initial color Color tone | Initial color YI-value | Color tone after irradiated with sun light for 10 min. |
|---|---|---|---|---|---|---|---|---|---|
| Ex.No. | | | | | | | | | |
| 94 | 29 | 0.08 | 1 | 0.05 | 1 | 0.04 | colorless | 2.41 | grey |
| 95 | 29 | 0.08 | 2 | 0.1 | 1 | 0.04 | colorless | 2.64 | brown |
| 96 | 29 | 0.08 | 2 | 0.09 | 2 | 0.03 | colorless | 2.58 | brown |
| 97 | 29 | 0.08 | 2 | 0.09 | 3 | 0.02 | colorless | 2.32 | brown |
| 98 | 31 | 0.06 | 1 | 0.08 | 4 | 0.06 | colorless | 2.55 | light brown |
| 99 | 31 | 0.1 | 1 | 0.04 | 5 | 0.02 | colorless | 2.62 | grey |
| 100 | 31 | 0.1 | 1 | 0.05 | 1 | 0.03 | colorless | 2.66 | grey |
| 101 | 31 | 0.04 | 1 | 0.1 | 1 | 0.15 | colorless | 2.11 | amber |
| 102 | 31 | 0.04 | 1 | 0.1 | 1 | 0.3 | colorless | 2.15 | violet grey |
| 103 | 1 | 0.05 | 2 | 0.02 | 5 | 0.01 | colorless | 1.88 | grey |
| 104 | 2 | 0.04 | 1 | 0.06 | 5 | 0.04 | colorless | 2.15 | brown |
| 105 | 3 | 0.05 | 1 | 0.08 | 1 | 0.04 | colorless | 3.99 | maroon brown |
| 106 | 5 | 0.08 | 2 | 0.04 | 1 | 0.03 | colorless | 4.01 | grey |
| 107 | 28 | 0.06 | 1 | 0.08 | 2 | 0.06 | colorless | 2.08 | brown |
| 108 | 29 | 0.08 | 2 | 0.04 | 1/5 | 0.02/0.02 | colorless | 2.45 | grey |
| 109 | 31 | 0.05 | 1 | 0.06 | 3/5 | 0.02/0.03 | colorless | 2.04 | brown |
| 110 | 29/31 | 0.05/0.05 | 1 | 0.08 | 2 | 0.02 | colorless | 2.46 | brown |

TABLE 5-continued
| Sample No. | Fulgimide compound No. | Amount of fulgimide (parts) | Chromene compound No. | Amount of chromene compound (parts) | Spiro-oxazine compound No. | Amount of spiro-oxazine compound (parts) | Initial color Color tone | Initial color YI-value | Color tone after irradiated with sun light for 10 min. |
|---|---|---|---|---|---|---|---|---|---|
| Comp.Ex.No. | | | | | | | | | |
| 15 | C | 0.08 | 1 | 0.07 | 1 | 0.04 | yellow | 19.84 | light brown |
| 16 | E | 0.1 | 1 | 0.05 | 1 | 0.03 | yellow | 20.56 | grey |
| 17 | G | 0.04 | 1 | 0.02 | 5 | 0.02 | yellow | 21.26 | grey |
(1)
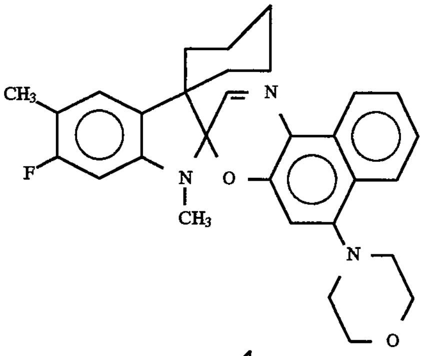
(2)
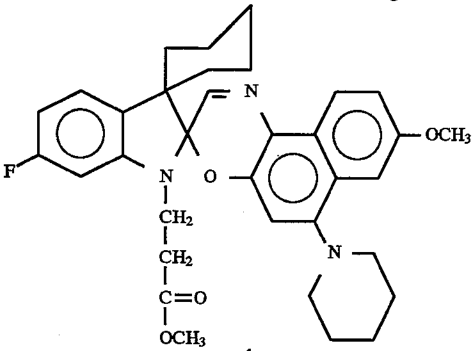
(3)
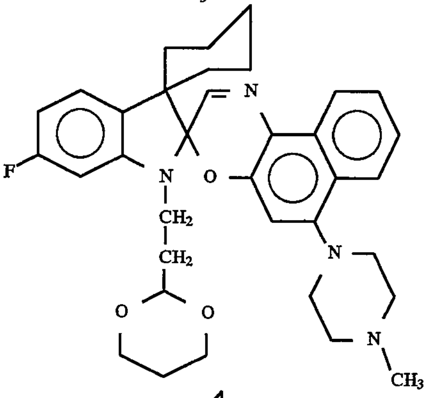
(4)
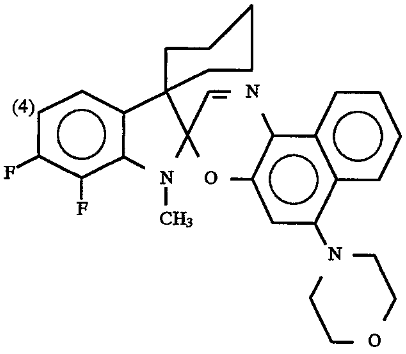

TABLE 5-continued

| Sample No. | Fulgimide compound No. | Amount of fulgimide (parts) | Chromene compound No. | Amount of chromene compound (parts) | Spiro-oxazine compound No. | Amount of spiro-oxazine compound (parts) | Initial color Color tone | Initial color YI-value | Color tone after irradiated with sun light for 10 min. |
|---|---|---|---|---|---|---|---|---|---|

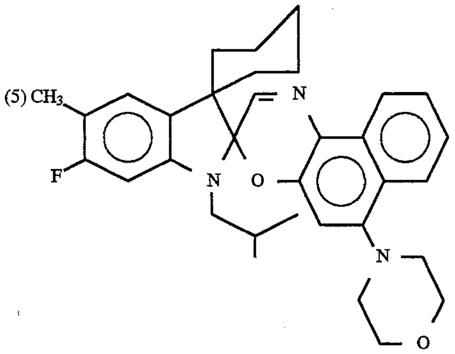

EXAMPLES 111 to 120

The fulgimide compounds and chromene compounds shown in Table 5 were mixed in amounts as shown in Table 5 into 100 parts of a polycarbonate resin, so that they were adsorbed on the surfaces of the resin. By using an injection molding machine, the resin was injection molded into a plate having a thickness of 2 mm. The molding was carried out a temperature of 270° C. The obtained molded plates were evaluated in the same manner as in Examples 67 to 93. The results were as shown in Table 3.

TABLE 6

| Sample No. | Fulgimide compound No. | Amount of fulgimide (parts) | Chromene compound No. | Amount of chromene compound (parts) | Initial color Color tone | Initial color YI-value | Color tone after irradiated with sun light for 10 min. |
|---|---|---|---|---|---|---|---|
| Ex. No. | | | | | | | |
| 111 | 29 | 0.1 | 2 | 0.1 | colorless | 5.78 | grey |
| 112 | 29 | 0.1 | 2 | 0.2 | colorless | 6.12 | brown |
| 113 | 29 | 0.2 | 1 | 0.1 | colorless | 7.34 | green |
| 114 | 29 | 0.5 | 2 | 0.5 | pale yellow | 10.56 | grey |
| 115 | 29 | 1.0 | 2 | 1.0 | pale yellow | 12.83 | grey |
| 116 | 29 | 3.0 | 2 | 6.0 | pale yellow | 18.56 | brown |
| 117 | 31 | 0.1 | 1 | 0.08 | colorless | 5.80 | grey |
| 118 | 29 | 0.1 | 1/2 | 0.05/0.03 | colorless | 5.92 | grey |
| 119 | 31 | 0.1 | 1/2 | 0.1/0.03 | colorless | 6.23 | amber |
| 120 | 1/2 | 0.05/0.05 | 1 | 0.15 | colorless | 6.85 | brown |
| Comp. Ex. No. | | | | | | | |
| 18 | E | 0.1 | 1 | 0.12 | yellow | 30.55 | grey |
| 19 | G | 0.1 | 2 | 0.1 | yellow | 33.21 | brown |

We claim:

1. A fulgimide compound represented by the following formula (I),

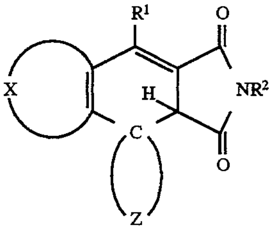

(I)

wherein the following formula (a)

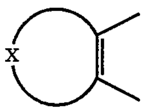

represents a divalent unsaturated heterocyclic group which may have a substituent, $R^1$ represents a monovalent hydrocarbon group or a monovalent heterocyclic group which may have a substituent, respectively, and the following formula (b),

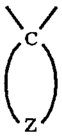

(b)

represents a norbornylidene group, bicyclo[3,3,1] nonylidene group or adamantylidene group which may have a substituent, respectively, and $R^2$ is a cyano group, alkoxycarbonyl group that may have a substituent, alkylcarbonyl group that may have a substituent, arylcarbonyl group that may have a substituent, nitro group, sulfonyl group, alkylsulfonyl group that may have a substituent, arylsulfonyl group that may have a substituent or aryloxycarbonyl group that may have a substituent.

2. A fulgimide compound according to claim 1, wherein the following formula (a),

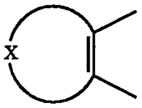

(a)

represents a divalent unsaturated heterocyclic group which may be substituted by at least one of halogen atom, nitro group, alkylthio group having 1 to 4 carbon atoms, aryl group having 6 to 10 carbon atoms, alkyl group having 1 to 4 carbon atoms or alkoxy group having 1 to 4 carbon atoms.

3. A fulgimide compound according to claim 2, wherein the following formula (a),

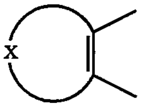

(a)

represents a five-membered or six-membered mono- heterocyclic group having at least one kind of hetero atom selected from nitrogen atom, oxygen atom or sulfur atom, or a condensed heterocyclic group obtained by condensing said heterocyclic group with a benzene ring or a cyclohexene ring, and which may be substituted by one to three halogen atoms, nitro groups, alkylthio groups having 1 to 4 carbon atoms, aryl groups having 6 to 10 carbon atoms, alkyl groups having 1 to 4 carbon atoms or alkoxy group having 1 to 4 carbon atoms depending upon their respective cases.

4. A fulgimide compound according to claim 1, wherein the following formula (b),

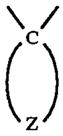

(b)

represents a norbornylidene group, a bicyclo[3,3,1] nonylidene group or an adamantylidene group which may be substituted by at least one of halogen atom, alkyl group having 1 to 4 carbon atoms or alkoxy group having 1 to 4 carbon atoms in their respective cases.

5. A fulgimide compound according to claim 1, wherein $R^1$ is an alkyl group having 1 to 20 carbon atoms, aryl group having 6 to 14 carbon atoms, cycloalkyl group having 3 to 7 carbon atoms, or five-membered or six-membered monoheterocyclic ring group having at least one kind of hetero atom selected from nitrogen atom, oxygen atom or sulfur atom, and which may have a substituent, respectively.

6. A fulgimide compound according to claim 1, wherein $R^2$ is a cyano group; an alkoxycarbonyl group which may be substituted by at least one of halogen atom or cyano group; an alkylcarbonyl group which may be substituted by at least one of halogen atom or cyano group; an arylcarbonyl group which may be substituted by at least one of halogen atom or cyano group; nitro group; sulfonyl group; an alkylsulfonyl group which may be substituted by at least one of halogen atom or cyano group; an arylsulfonyl group which may be substituted by at least one of halogen atom or cyano group; or an aryloxycarbonyl group which may be substituted by at least one of halogen atom or cyano group.

7. A fulgimide compound according to claim 6, wherein $R^2$ is a cyano group; an alkoxycarbonyl group having 2 to 5 carbon atoms which may be substituted by at least one of halogen atom or cyano group; an alkylcarbonyl group having 2 to 5 carbon atoms which may be substituted by at least one of halogen atom or cyano group; an arylcarbonyl group having 7 to 11 carbon atoms which may be substituted by at least one of halogen atom or cyano group; nitro group; sulfonyl group; an alkylsulfonyl group having 1 to 4 carbon atoms which may be substituted by at least one of halogen atom or cyano group; an arylsulfonyl group having 6 to 10 carbon atoms which may be substituted by at least one of halogen atom or cyano group; or an aryloxycarbonyl group having 7 to 11 carbon atoms which may be substituted by at least one of halogen atom or cyano group.

* * * * *